United States Patent
Locklin et al.

(10) Patent No.: US 9,714,481 B2
(45) Date of Patent: Jul. 25, 2017

(54) PHOTOCHEMICAL CROSS-LINKABLE POLYMERS, METHODS OF MAKING PHOTOCHEMICAL CROSS-LINKABLE POLYMERS, METHODS OF USING PHOTOCHEMICAL CROSS-LINKABLE POLYMERS, AND METHODS OF MAKING ARTICLES CONTAINING PHOTOCHEMICAL CROSS-LINKABLE POLYMERS

(75) Inventors: Jason J. Locklin, Bogart, GA (US); Vikram Dhende, Summerville, SC (US)

(73) Assignee: THE UNIVERSITY OF GEORGIA RESEARCH FOUNDATION, INC, Athens, GA (US)

( * ) Notice: Subject to any disclaimer, the term of this patent is extended or adjusted under 35 U.S.C. 154(b) by 583 days.

(21) Appl. No.: 13/643,411

(22) PCT Filed: Apr. 28, 2011

(86) PCT No.: PCT/US2011/034268
§ 371 (c)(1),
(2), (4) Date: Oct. 25, 2012

(87) PCT Pub. No.: WO2011/139817
PCT Pub. Date: Nov. 10, 2011

(65) Prior Publication Data
US 2013/0040519 A1 Feb. 14, 2013

Related U.S. Application Data

(60) Provisional application No. 61/328,879, filed on Apr. 28, 2010, provisional application No. 61/370,919, filed on Aug. 5, 2010.

(51) Int. Cl.
| | | |
|---|---|---|
| C08F 2/46 | (2006.01) |
| C08G 61/04 | (2006.01) |
| D06M 13/48 | (2006.01) |
| B32B 7/10 | (2006.01) |
| B32B 27/08 | (2006.01) |
| C08G 73/02 | (2006.01) |
| C08J 7/12 | (2006.01) |
| C08L 79/02 | (2006.01) |
| D06M 15/61 | (2006.01) |
| B32B 5/02 | (2006.01) |
| B32B 7/12 | (2006.01) |
| B32B 27/12 | (2006.01) |
| B32B 27/28 | (2006.01) |

(52) U.S. Cl.
CPC ............ *D06M 13/48* (2013.01); *B32B 5/02* (2013.01); *B32B 7/10* (2013.01); *B32B 7/12* (2013.01); *B32B 27/08* (2013.01); *B32B 27/12* (2013.01); *B32B 27/281* (2013.01); *C08G 73/0226* (2013.01); *C08J 7/123* (2013.01); *C08L 79/02* (2013.01); *D06M 15/61* (2013.01); *B32B 2307/538* (2013.01); *B32B 2307/7145* (2013.01); *B32B 2307/732* (2013.01); *B32B 2439/70* (2013.01); *B32B 2553/00* (2013.01); *C08J 2479/08* (2013.01); *Y10T 428/249991* (2015.04); *Y10T 428/265* (2015.01); *Y10T 428/2938* (2015.01); *Y10T 428/31504* (2015.04); *Y10T 428/31649* (2015.04); *Y10T 428/31699* (2015.04); *Y10T 428/31935* (2015.04); *Y10T 442/2525* (2015.04)

(58) Field of Classification Search
None
See application file for complete search history.

(56) References Cited

U.S. PATENT DOCUMENTS

| | | | |
|---|---|---|---|
| 3,265,772 A | 8/1966 | Tocker | |
| 3,697,402 A | 10/1972 | Clifton et al. | |
| 3,998,855 A * | 12/1976 | Karrer .................... | C07C 45/71 424/DIG. 8 |
| 4,011,266 A | 3/1977 | Pearson et al. | |
| 4,659,572 A * | 4/1987 | Murray ......................... | 424/448 |
| 5,106,878 A * | 4/1992 | Guerry et al. ................ | 514/651 |
| 5,714,360 A * | 2/1998 | Swan et al. .................. | 435/174 |
| 5,723,513 A | 3/1998 | Bonham et al. | |
| 7,709,544 B2 | 5/2010 | Doyle et al. | |
| 8,114,319 B2 | 2/2012 | Davis et al. | |
| 8,183,540 B2 | 5/2012 | Ward et al. | |
| 2003/0236425 A1* | 12/2003 | Herr ...................... | C07F 7/0852 556/443 |

(Continued)

FOREIGN PATENT DOCUMENTS

| | | |
|---|---|---|
| GB | 972971 A | 10/1964 |
| WO | 2010096444 | 8/2010 |
| WO | 2010096444 A2 | 8/2010 |

OTHER PUBLICATIONS

Sanchez-Ferrer et al, Photo-crosslinked Side-Chain Liquid-Crystalline Elastomers for Microsystems, Macromol. Chem. Phys., 2009, 210, 1671-1677.*

(Continued)

*Primary Examiner* — Jessica E Whiteley
(74) *Attorney, Agent, or Firm* — Thomas|Horstemeyer, LLP

(57) ABSTRACT

Polymer compositions, methods of making polymer compositions, structures having the polymer composition covalently bonded to the surface of the structure, methods of attaching the polymer to the surface of the structure, methods of decreasing the amount of microorganisms formed on a structure, and the like, are disclosed.

10 Claims, 12 Drawing Sheets

(56) References Cited

U.S. PATENT DOCUMENTS

| | | |
|---|---|---|
| 2006/0105012 A1 | 5/2006 | Chinn et al. |
| 2006/0135639 A1 | 6/2006 | Singh |
| 2006/0147413 A1 | 7/2006 | Alferiev et al. |
| 2006/0148982 A1 | 7/2006 | Ijeoma et al. |
| 2007/0054119 A1 | 3/2007 | Garstecki et al. |
| 2007/0231291 A1 | 10/2007 | Huang et al. |
| 2008/0025503 A1 | 1/2008 | Choi et al. |
| 2009/0162767 A1 | 6/2009 | Wu |
| 2009/0196826 A1 | 8/2009 | Gao et al. |
| 2010/0178512 A1 | 7/2010 | Giesenberg et al. |
| 2011/0034585 A1 | 2/2011 | Christmann et al. |
| 2011/0081643 A1 | 4/2011 | Fournier-Bidoz et al. |
| 2011/0294384 A1 | 12/2011 | Locklin et al. |
| 2013/0183246 A1 | 7/2013 | Wang et al. |

OTHER PUBLICATIONS

Office Action in related Chinese Application No. 201080008259.0 dated Jun. 18, 2013.
Extended European Search Report dated Oct. 18, 2013.
The International Search Report and Written Opinion dated Sep. 16, 2010.
Goyal; Nanoscale Approaches for Biomolecule Separtion and Detection. Master in Science in Biomedical Engineering Requirement—Graduate School of The University of Texas at Arlington. Dec. 2009.
Dendukuri, et al.; The Synthesis and Assembly of Polymeric Microparticles Using Microfluidics. Advanced Review. vol. 21, 2009. 2009 WILEY-VCH Verlag GmbH & Co. KGaA, Weinheim pp. 4071-4086.
Yuan, et al.; Large scale manufacture of magnetic polymer particles using membranes and microfluidic devices. China Particuology. vol. 5, 2007. pp. 26-42.
Chen, et al., Microfluidic Assembly of Magnetic Hydrogel Particles with Uniformly Anisotropic Structure. Advanced Review. vol. 21, 2009. 2009 WILEY-VCH Verlag GmbH & Co. KGaA, Weinheim pp. 3201-3204.
Hwang, et al., Microfluidic-based synthesis of non-spherical magnetic hydrogel microparticles. Lab on a Chip. vol. 8, 2008. The Royal Society of Chemistry 2008 pp. 1640-1647.
Shum, et al.; Droplet Microfluidics for Fabrication of Non-Spherical Particles. Macromolecular Rapid Communications. vol. 32, 2010. 2010 WILEY-VCH Verlag GmbH & Co. KGaA, Weinheim. pp. 108-118.
Wang, et al.; Fabrication of Monodisperse Toroidal Particles by Polymer Solidification in Microfluidics. ChemPhysChem. vol. 10, 2009. 2009 WILEY-VCH Verlag GmbH & Co. KGaA, Weinheim, pp. 641-645.
The International Preliminary Report on Patentability dated Nov. 8, 2012.
Denmark Se, et al. Org. Synth. 2009, vol. 86, p. 274.
Oh JK, et al. J. Polym. Sci. A Polym. Chem., 2002, vol. 40(17), p. 3001.
Further Examination Report, NZ 602911, dated Jul. 7, 2014.
Supplementary European Search Report, EP 11777997, dated Jun. 26, 2014.
Examination Report on related New Zealand Application No. 602911 dated Jun. 18, 2013.
The International Search Report and Written Opinion dated Jan. 19, 2012.
Office Action mailed Dec. 29, 2016. U.S. Appl. No. 14/351,348.

* cited by examiner

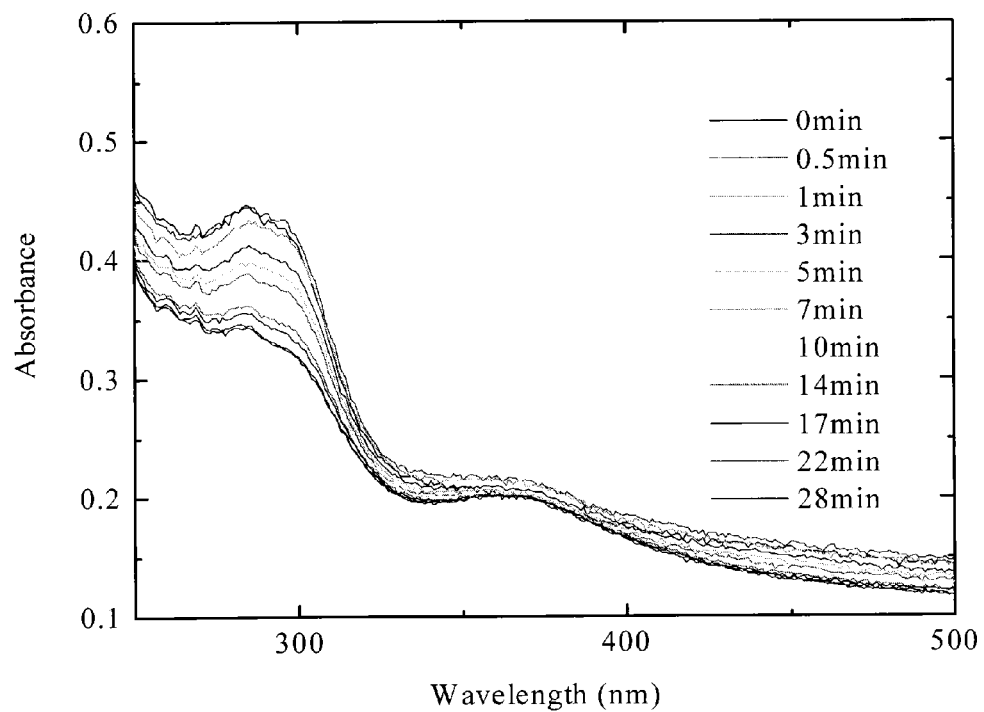
FIG. 1.1
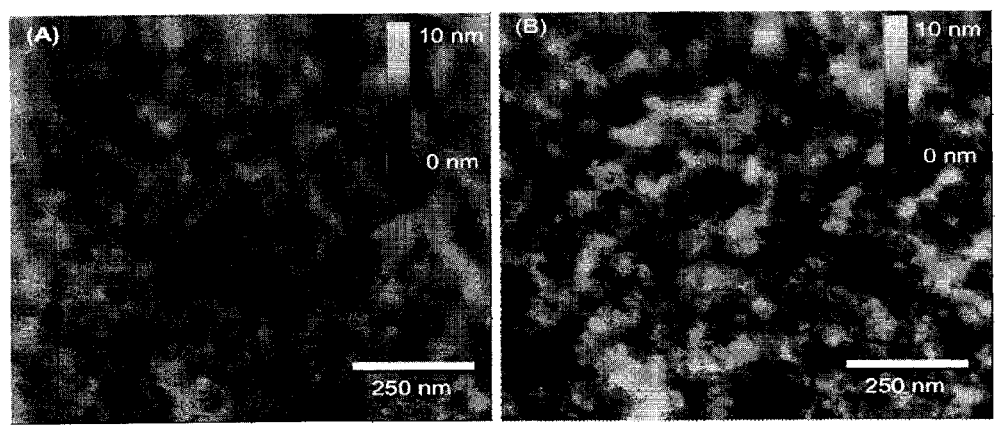
FIG. 1.2    FIG. 1.3

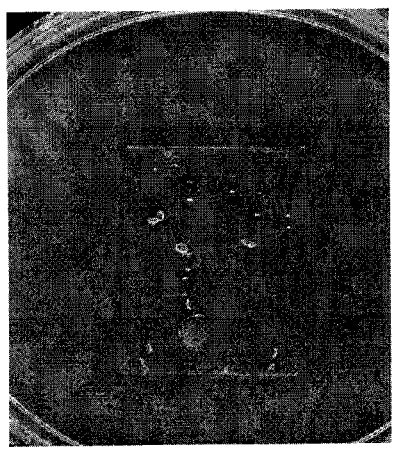
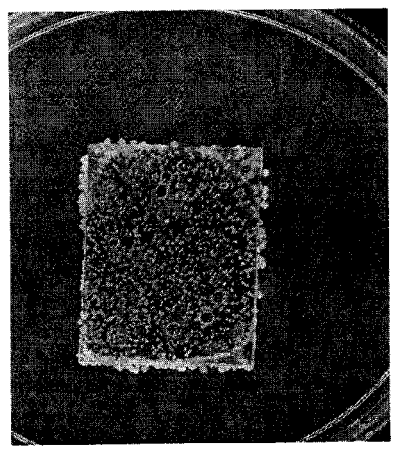
FIG. 1.4
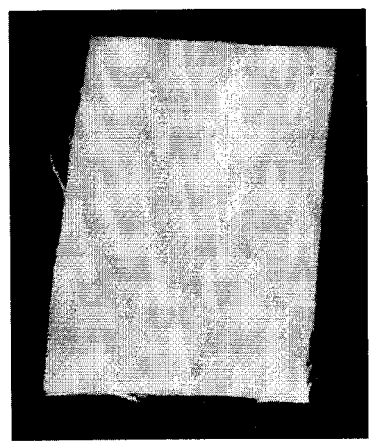
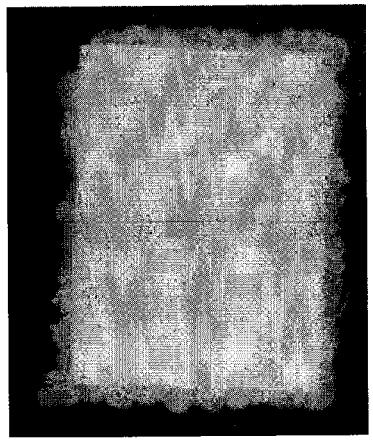
FIG. 1.5

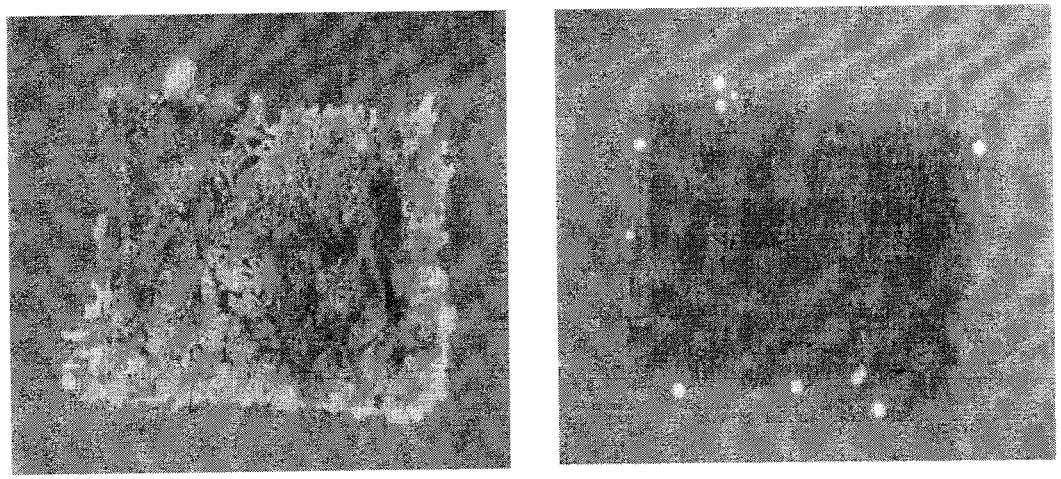
FIG. 1.6
FIG. 1.7

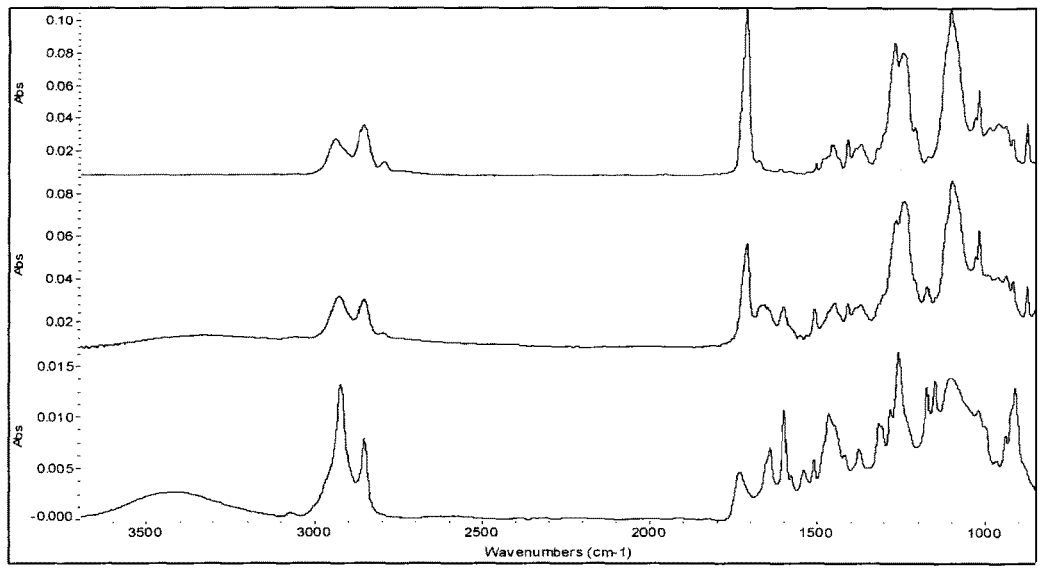
FIG. 2.1
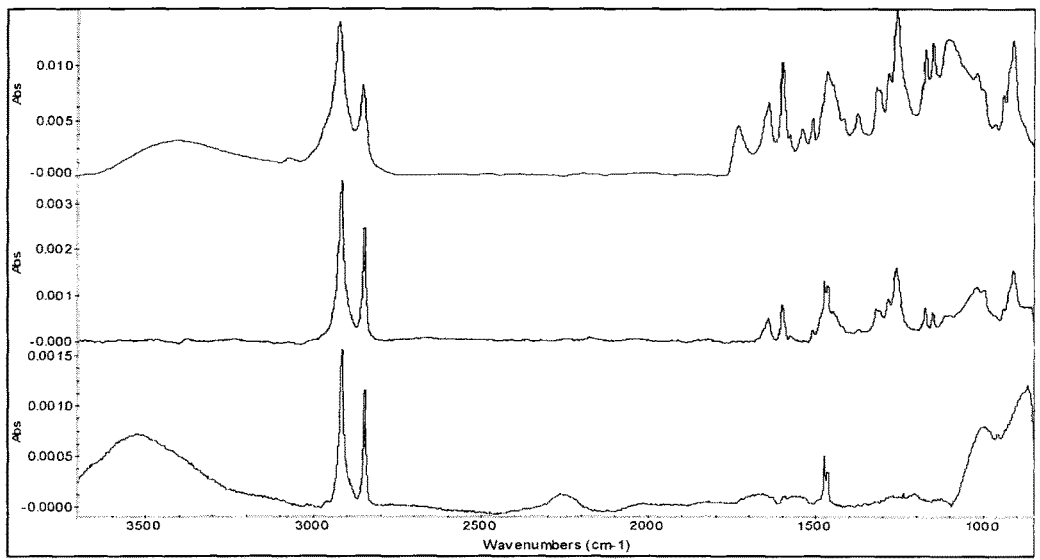
FIG. 2.2

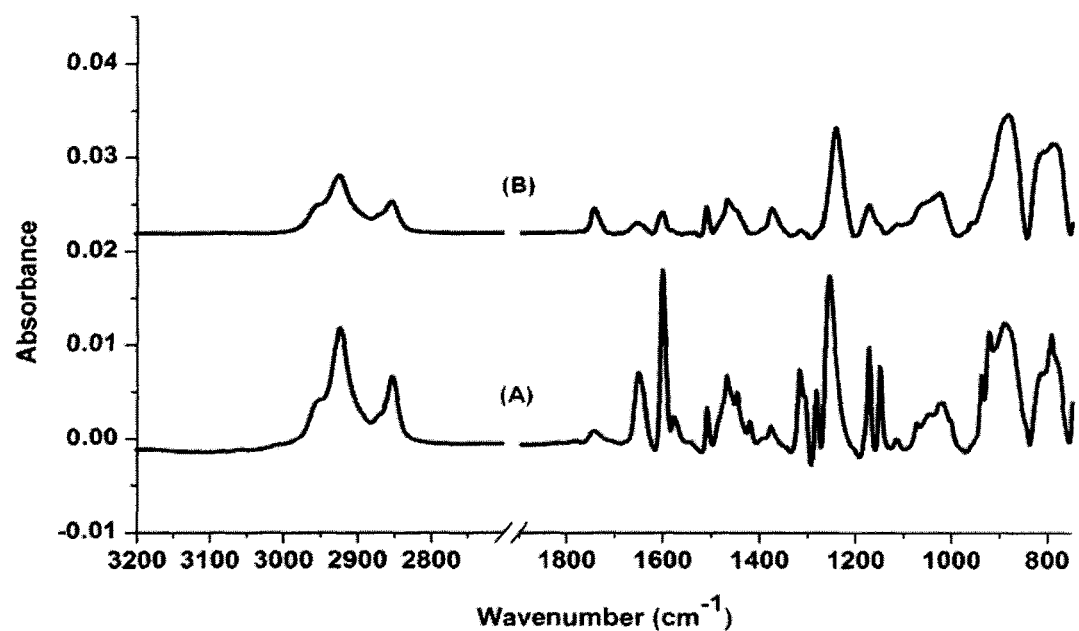
FIG. 3.1

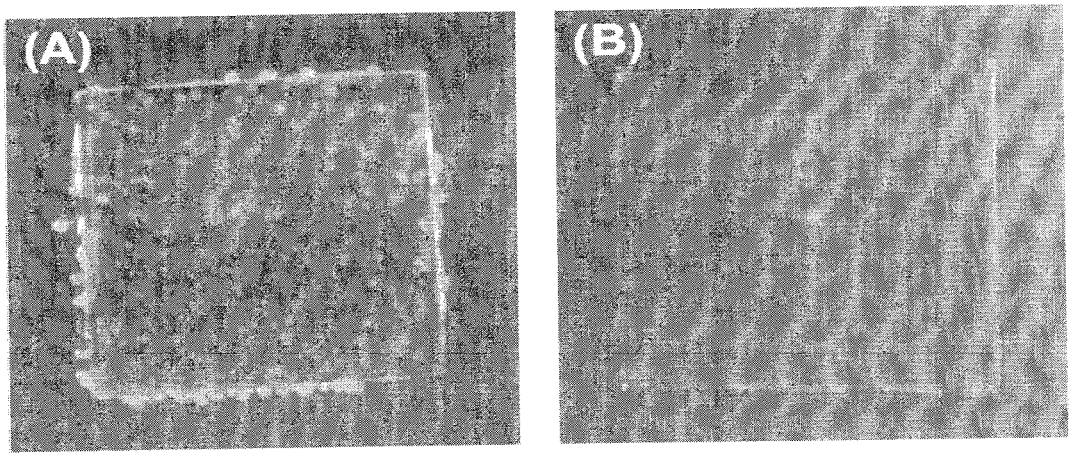
FIG. 3.2
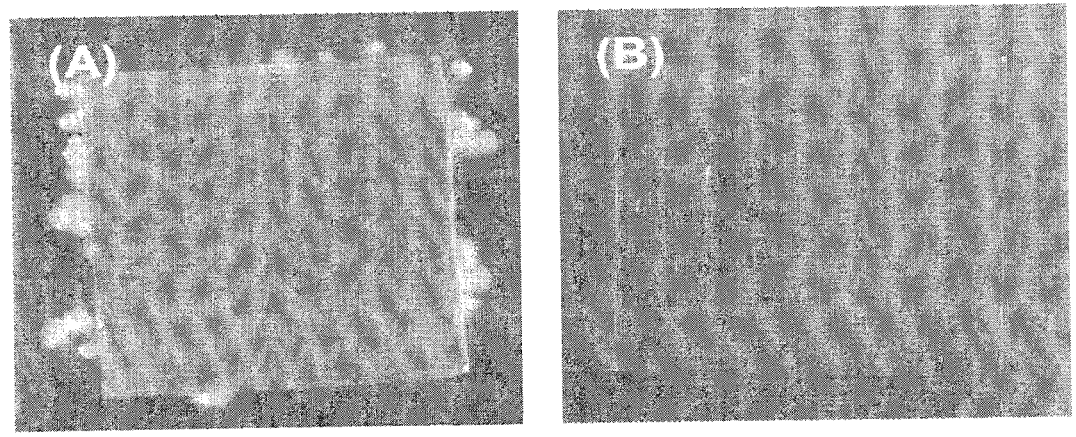
FIG. 3.3

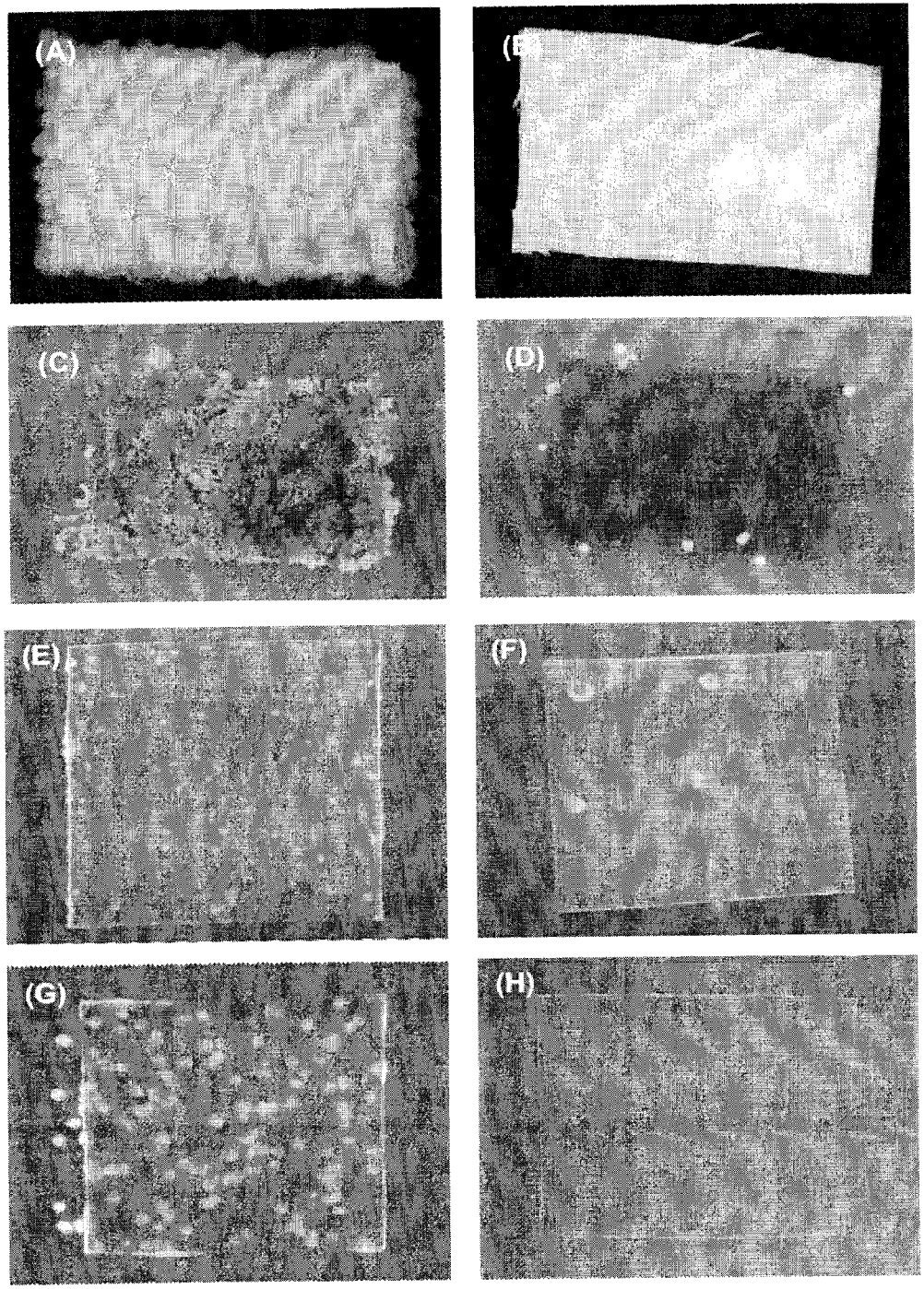
FIG. 3.4

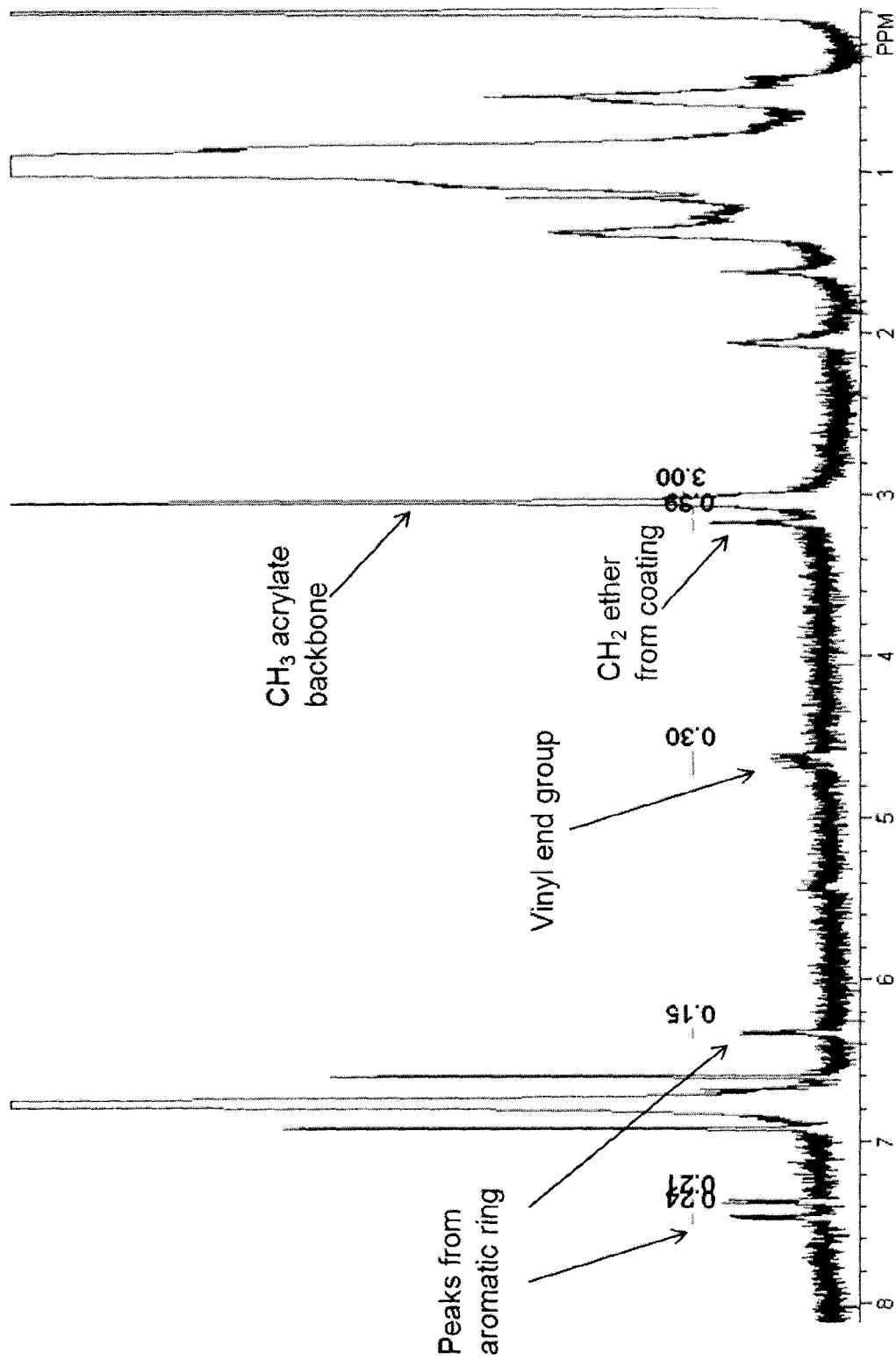
FIG. 4.1

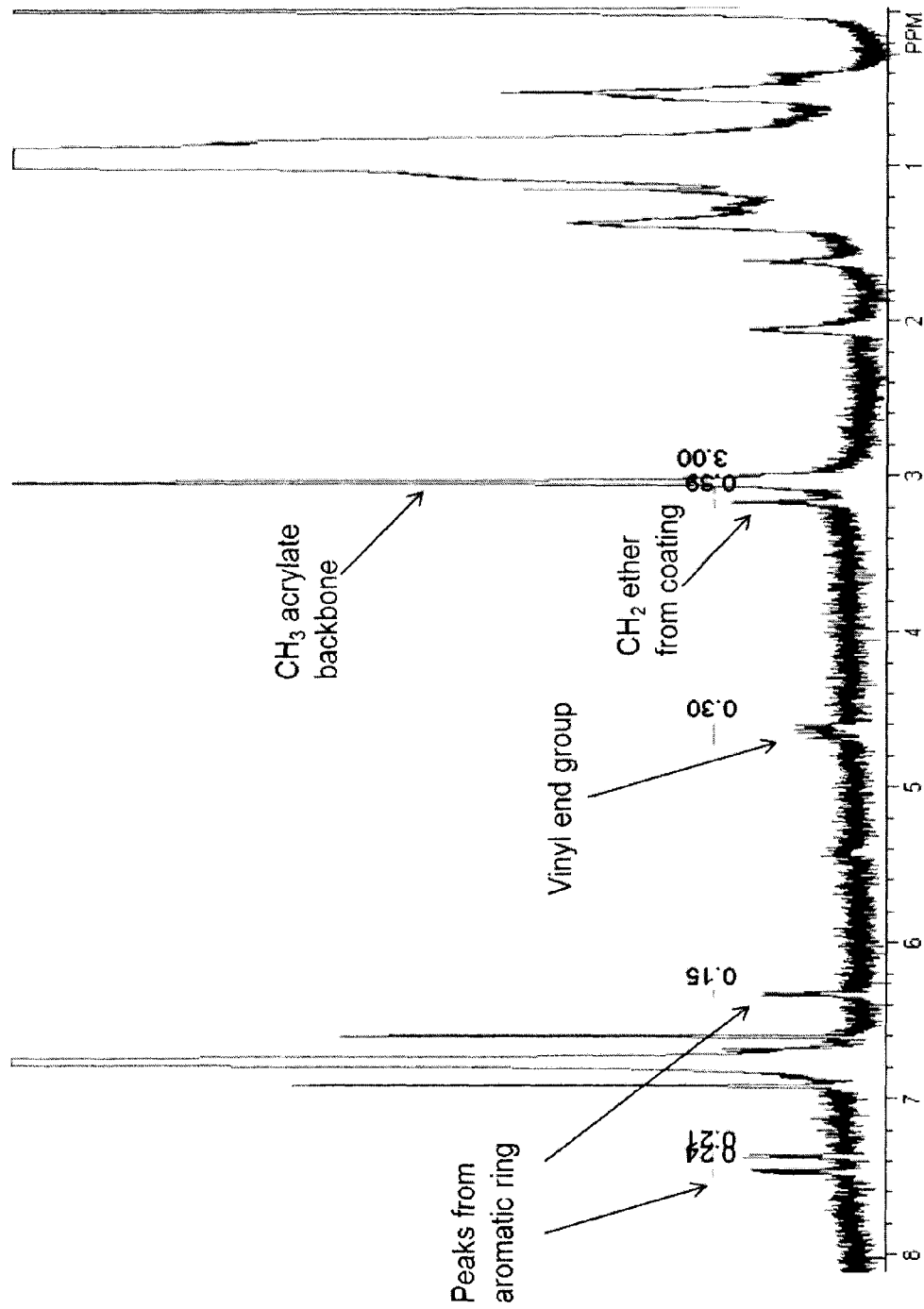
FIG. 4.2

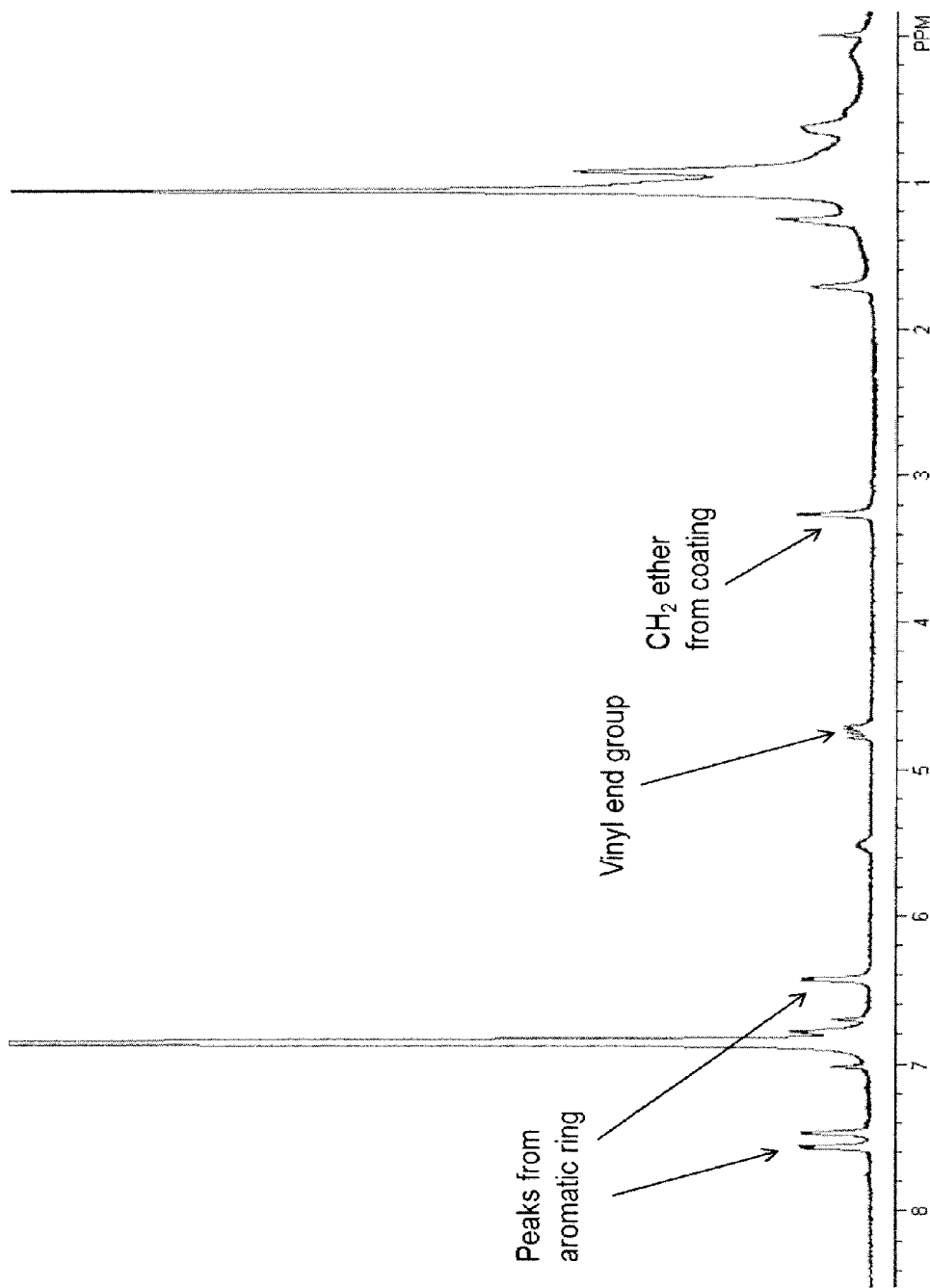
FIG. 4.3

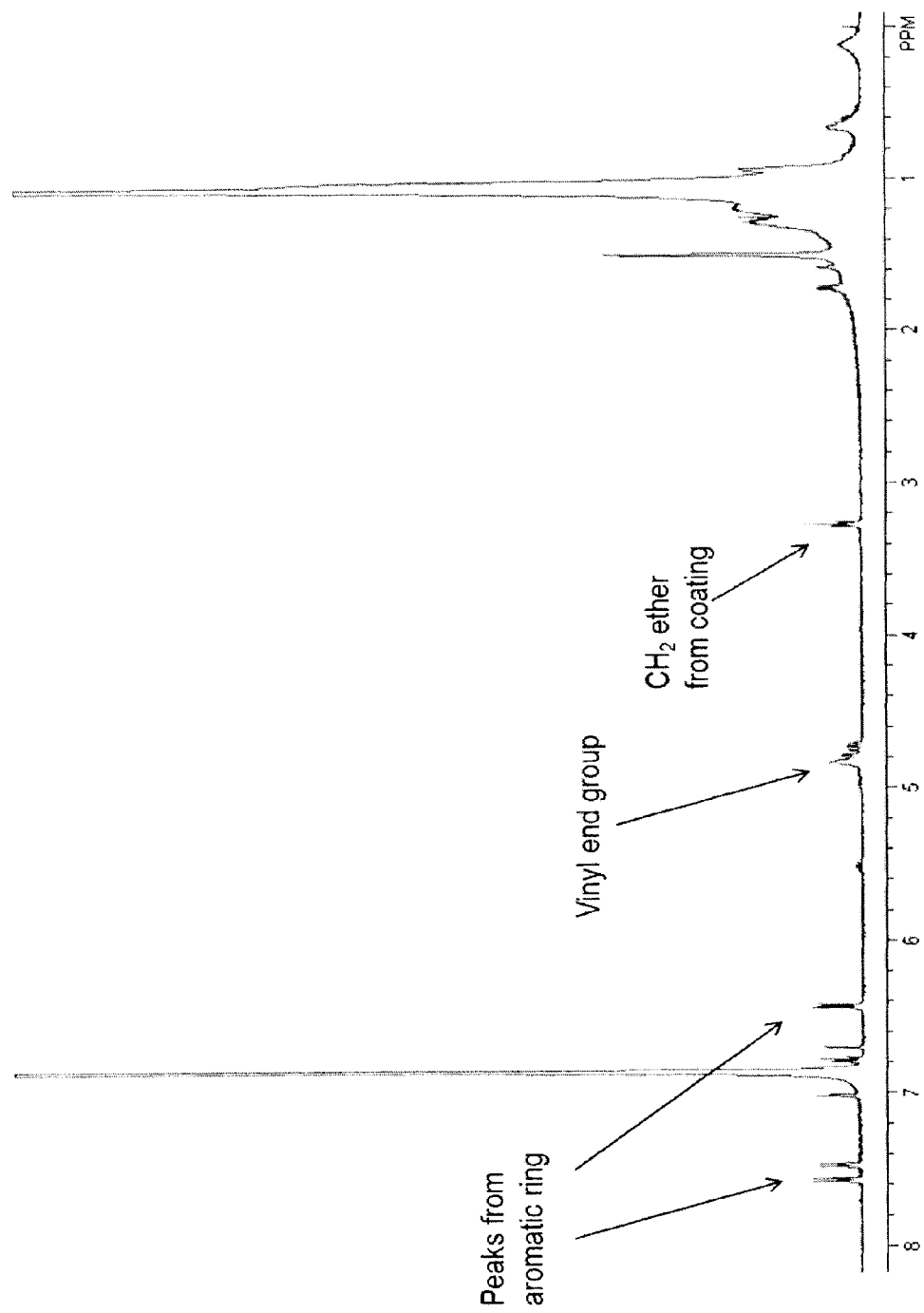
FIG. 4.4

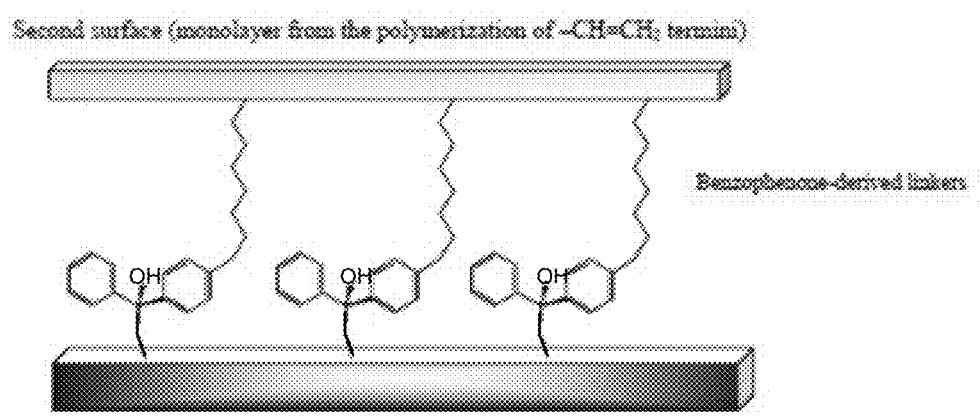
FIG. 5.1

PHOTOCHEMICAL CROSS-LINKABLE POLYMERS, METHODS OF MAKING PHOTOCHEMICAL CROSS-LINKABLE POLYMERS, METHODS OF USING PHOTOCHEMICAL CROSS-LINKABLE POLYMERS, AND METHODS OF MAKING ARTICLES CONTAINING PHOTOCHEMICAL CROSS-LINKABLE POLYMERS

CROSS REFERENCE TO RELATED APPLICATION

This application is the 35 U.S.C. §371 national stage of PCT application having serial number PCT/US2011/034268, filed on Apr. 28, 2011. This application also claims priority to and benefit of U.S. Provisional Application No. 61/328,879 filed on Apr. 28, 2010 and U.S. Provisional Application No. 61/370,919, filed on Aug. 5, 2010, each of which are incorporated by reference in their entireties.

BACKGROUND

Microbial infection is one of the most serious concerns for many commercial applications such as textiles, food packaging and storage, shoe industry, water purification, medical devices, and dental surgery equipment. Recently, antimicrobial agents have gained significant interest from both an academic and industrial point of view because of their potential to provide safety benefits to a diverse range of materials. Thus, there is a need to discover antimicrobial agents that address current needs.

SUMMARY

Polymer compositions, methods of making polymer compositions, structures having the polymer composition covalently bonded to the surface of the structure, methods of attaching the polymer to the surface of the structure, methods of decreasing the amount of microorganisms formed on a structure, and the like, are disclosed.

An exemplar embodiment of a polymer, among others, includes a linear or branched polyethylenimine polymer that has been quaternized with a hydrophobic side chain moiety and a photo cross-linkable moiety.

An exemplar embodiment of a method of disposing a polymer on a surface, among others, includes: providing a polymer of the present disclosure; disposing the polymer on a structure having a surface having C—H groups; and exposing the polymer to a UV light, wherein the interaction of the polymer with the UV light causes the polymer to covalently bond with the surface An exemplar embodiment of a structure, among others, includes: a surface having a polymer of the present disclosure covalently attached to the surface, wherein the structure has an antimicrobial characteristic.

An exemplar embodiment of a material, among others, includes: a vinyl moiety and a photo cross-linkable moiety.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 illustrates the change in UV spectra of a benzophenone side-chain in polymer 2b (or 2 in Example V) with UV exposure time (365 nm).

FIG. 1.2 illustrates an AFM image for the film of polymer 2b (or 2 in Example V) (122 nm) before sonication with an RMS roughness of 0.48 nm.

FIG. 1.3 illustrates an AFM image for the film of polymer 2b (or 2 in Example V) (65 nm) after sonication with RMS roughness of 0.83 nm.

FIG. 1.4 illustrates digital pictures of glass substrates that were sprayed with *Staphylococcus. Aureus*. (left) control slide and (right) 65 nm thick polymer 2b.

FIG. 1.5 illustrates digital pictures of cotton strips that were sprayed with *Staphylococcus Aureus*. (left) control and (right) substrate spray coated with cross-linked polymer 2b.

FIG. 1.6 illustrates digital pictures of a polypropylene non-woven geotextiles that were sprayed with *Staphylococcus aureus*. (left) control and (right) substrate spray coated with cross-linked polymer 2b.

FIG. 1.7 illustrates digital pictures of polyvinylchloride coated polyester grid structures that were sprayed with *Staphylococcus aureus* (left) control and (right) substrate sponge dabbed with cross-linked polymer 2b solution (15 mg/ml) and laundered.

FIG. 2.1 illustrates an FTIR spectra of top: Hytrel-4056; middle: Hytrel coated with PEI copolymer; bottom: PEI copolymer.

FIG. 2.2 illustrates an FTIR spectra of top: PEI copolymer; middle: Petrothane coated with PEI copolymer; bottom: Petrothene.

FIG. 3.1 illustrates an FTIR spectra of a thin film of copolymer 2 before (A) and after (B) UV exposure.

FIG. 3.2 illustrates digital pictures of the glass substrates sprayed with *S. aureus* and incubated for 24 hours at 37° C.: FIG. 3.2A is a control substrate and FIG. 3.2B is a glass substrate modified with polymer 2 after sonication.

FIG. 3.3 illustrates digital pictures of the glass substrates sprayed with *E. coli*: FIG. 3.3A is a control substrate and FIG. 3.3B is glass substrate modified with 2 after sonication.

FIG. 3.4 illustrates digital pictures of the textiles and plastic substrates sprayed with *S. aureus*: FIG. 3.4A, untreated cotton, FIG. 3.4B, cotton sprayed coated with 15 mg/ml polymer 2, FIG. 3.4C, untreated polypropylene (non-woven geotextile fabric), FIG. 3.4AD, polypropylene spray-coated with 15 mg/ml polymer 2, FIG. 3.4E, untreated poly(vinyl chloride) substrate, FIG. 3.4F, poly(vinyl chloride) substrate spray coated with 15 mg/ml polymer 2, FIG. 3.4G, untreated polyethylene substrate, and FIG. 3.4H, polyethylene substrate spray coated with 15 mg/ml polymer 2.

FIG. 4.1 illustrates a proton NMR of ethylene-methyl acrylate copolymer (Optema TC115) coated with modified BP, coating to substrate ratio (33:100).

FIG. 4.2 illustrates a proton NMR of ethylene-methyl acrylate copolymer (Optema TC 115) coated with modified BP, coating to substrate ratio (5:100).

FIG. 4.3 illustrates a proton NMR of polyethylene (SABIC 2100) coated with modified BP, coating to substrate ratio (5:100).

FIG. 4.4 illustrates a proton NMR of ethyl vinyl acetate copolymer (Elvax® 460) coated with modified BP, coating to substrate ratio (5:100).

FIG. 5.1 illustrates two surfaces bound to one another by diphenylmethoxy groups.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "substituted" refers to any one or more hydrogens on the designated atom that can be replaced with a selection from the indicated group, provided that the designated atom's normal valence is not exceeded, and that the substitution results in a stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Carnesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxefla, Butyrivibrio, Calymmatobacterium, Campylobacter, Capnocytophaga, Cardiobacterium, Catonefia, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenefla, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserefla, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Trophetyma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella bumetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other Enterobacteria, *Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae*.

The term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia*.

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena* sp., *Prymnesium* sp., *Porphyridium* sp., *Synechoccus* sp., *Botryococcus braunii, Crypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp., *Senedesmus obliquus,* and *Tetraselmis sueica* as well as algae belonging to any of *Spirogyra, Cladophora, Vaucheria, Pithophora* and *Enteromorpha* genera.

The term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

As used herein, the term "fiber" refers to filamentous material that can be used in fabric and yarn as well as textile fabrication. One or more fibers can be used to produce a fabric or yarn. Fibers include, without limitation, materials such as cellulose, fibers of animal origin (e.g., alpaca, angora, wool and vicuna), hemicellulose, lignin, polyesters, polyamides, rayon, modacrylic, aramids, polyacetates, polyxanthates, acrylics and acrylonitriles, polyvinyls and functionalized derivatives, polyvinylidenes, PTFE, latex, polystyrene-butadiene, polyethylene, polyacetylene, polycarbonates, polyethers and derivatives, polyurethane-polyurea copolymers, polybenzimidazoles, silk, lyocell, carbon fibers, polyphenylene sulfides, polypropylene, polylactides, polyglycolids, cellophane, polycaprolactone, "M5"

(poly{diimidazo pyridinylene (dihydroxy)phenylene}), melamine-formadehyde, plastarch, PPOs (e.g., Zylon®), polyolefins, and polyurethane.

The term "textile article" can include garments, fabrics, carpets, apparel, furniture coverings, drapes, upholstery, bedding, automotive seat covers, fishing nets, rope, articles including fibers (e.g., natural fibers, synthetic fibers, and combinations thereof), articles including yarn (e.g., natural fibers, synthetic fibers, and combinations thereof), and the like.

Discussion:

In accordance with the purpose(s) of the present disclosure, as embodied and broadly described herein, embodiments of the present disclosure, in one aspect, relate to polymer compositions, methods of making polymer compositions, structures having the polymer composition covalently bonded to the surface of the structure, methods of attaching the polymer to the surface of the structure, methods of decreasing the amount of microorganisms formed on a structure, and the like. In an embodiment, the polymer composition (or the polymer disposed on a surface) may have an antimicrobial characteristic (e.g., kills at least 70%, at least 80%, at least 90%, at least 95%, or at least 99% of the microorganisms (e.g., bacteria) on the surface and/or reduces the amount of microorganisms that form or grow on the surface by at least 70%, at least 80%, at least 90%, at least 95%, or at least 99%, as compared to a similar surface without the polymer composition disposed on the surface). In an embodiment, the polymer composition (or the polymer disposed on a surface of a structure) may not have an antimicrobial characteristic. Additional details are described in Examples I to VI.

In an embodiment, the structures can include those that may be exposed to microorganisms and/or that microorganisms can grow on such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. The structures may also include live biologic structures (or surfaces of live biologic structures) such as seeds for agricultural uses, tree limbs, and trunk, as well as teeth. In an embodiment, the structure inherently includes C—H groups on the surface of the structure to interact with the polymer, as described below. In an embodiment, the structure includes a functionalized layer disposed on the structure that includes the C—H groups on the surface to interact with the polymer. In an embodiment, the structure can include surfaces that inherently include C—H groups on the surface of the structure and also can include surfaces that include a functionalized layer disposed on the structure that includes the C—H groups. In an embodiment, the functionalized layer can have a thickness of about 2 nanometers (nm) to 1 micrometer (µm) or about 25 nm to 120 nm.

In an embodiment, the structure can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures having a functionalized layer (e.g., includes a C—H group) on the surface of the structure, metals, metal alloys, or metal oxides structure having a functionalized layer (e.g., includes a C—H group) on the surface of the structure, a structure (e.g., tile, stone, ceramic, marble, granite, or the like) having a functionalized layer (e.g., includes a C—H group) on the surface of the structure, and a combination thereof. In an embodiment, the structure includes structures used in the fishing industry and these include fishing nets, fishing gear and tackle, fish, crab or lobster cages, and the like.

In an embodiment, the polymer is covalently bonded via the interaction of the polymer with a UV light (e.g., about 340 to 370 nm) that causes a C—C bond to form between the polymer and the surface having a C—H group or a layer on the surface having the C—H group. In other words, the polymer can be attached to the surface or the layer on the surface through a photochemical process so the bonding is easy and inexpensive to achieve. Once the covalent bonds are formed, the polymer layer is strongly bound to the surface and can withstand very harsh conditions such as sonication and extended washing steps as well as exposure to harsh environmental conditions (e.g., heat, cold, humidity, lake, river, and ocean conditions (e.g., above and/or under water), and the like).

In an embodiment, the polymer (also referred to as a "polymer composition") includes a linear or branched polyethyleneimine polymer that has been quaternized with a hydrophobic side chain moiety and a photo cross-linkable moiety. In an embodiment, the molar ratio between hydrophobic side chain moiety and photo cross-linkable moiety can be about 99:1 to 10:90 including about 20:80, about 30:70, about 50:50, about 70:30, about 80:20, ranges between each of these and other ratios in between. In an embodiment, the polyethyleneimine polymer is a linear polyethyleneimine polymer that can include secondary amines. In an embodiment, the polyethyleneimine polymer is a branched polyethyleneimine polymer that can include primary, secondary, and/or tertiary amino groups.

In an embodiment, the polymer can have the following structure

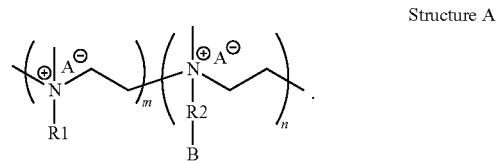

Structure A

The polyethyleneimine polymer can be linear or branched. R1 is a hydrophobic side chain moiety and is B a photo cross-linkable moiety. A is a counter ion and R2 is a linking moiety such as a hydrocarbon carbon chain (e.g., saturate or unsaturated, and optionally substituted).

In an embodiment, the polymer can have the following structure (Scheme 1):

Example of Possible Branching Structures in Branched Copolymer

Linear Copolymer

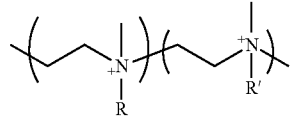

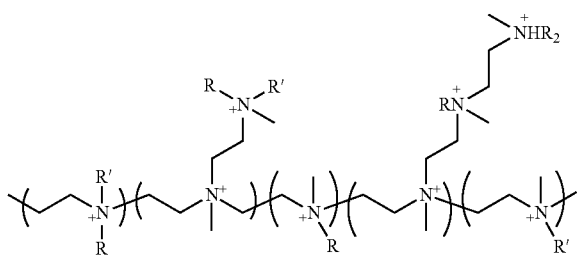

R=alkyl chain such as

R'=alkyl chain with benzophenone derivative such as

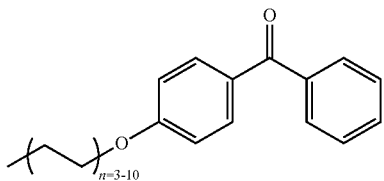

Scheme 1

The above structure is for illustrative, non-limiting purposes. The structure of the polymer may take on other branching patterns, or comprise single or multiple sites for attachment to surfaces through a photochemical reaction. Schemes 2-3 below illustrate the formation of a polymer and attachments to a surface. Scheme 4 below describes how the polymer attaches to a surface. Additional details are provided in Examples I to VI.

In an embodiment, the counter anion (e.g., A) on quaternary amine polymers can include different anions such as chloride, bromide, iodide, alkyl sulfate anions (e.g., methyl sulfate, ethyl sulfate, dodecylsulfate), tetrafluoroborate, and tosylate.

In an embodiment, the polymer composition that includes a linear or branched polyethyleneimine polymer that has been quaternized with a hydrophobic side chain moiety and a photo cross-linkable moiety, is blended with another, secondary polymer to form a polymer blend that can be directly used to manufacture polymers or polymer-based items or as a surface treatment, wherein (i) the secondary polymer can be any thermosetting or thermoplastic polymer, a finish material such as a resin or an adhesive, or other polymer cited herein or (ii) the secondary polymer of (i) may include an optional colored pigment.

In an embodiment, the polymer can have a molecular weight of about 20 kilodaltons to 5000 kilodaltons. In an embodiment, the polymer can have a molecular weight of about 50 kilodaltons to 1000 kilodaltons. In an embodiment, the polymer can have a molecular weight of about 50 kilodaltons to 500 kilodaltons. In an embodiment, the polymer can have a molecular weight of about 50 kilodaltons to 250 kilodaltons. In an embodiment, the polymer can have a molecular weight of about 50 kilodaltons to 150 kilodaltons. In an embodiment, the polymer can have a molecular weight of about 100 kilodaltons to 150 kilodaltons.

In an embodiment, the hydrophobic side chain moiety (e.g., R1) functions to at least provide a hydrophobic characteristic to the polymer. In an embodiment, the hydrophobic side chain can include a hydrocarbon chain such as: octane or its derivatives (e.g., 2-ethylhexane, 3-(methyl) heptane, 6-methylheptane, 2-methylheptane), decane or its derivatives (e.g., 3,7-dimethyl octane, 7-methyl nonane), dodecane or its derivatives (e.g., 4,8-dimethyl decane, 2-methyl undecane, 3-methyl undecane, 9-methyl undecane, 10-methyl undecane), tridecane or its derivatives (e.g., 2-methyl dodecane, 3-methyl dodecane, 6-methyl dodecane, 7-methyl dodecane, 8-methyl dodecane, 9-methyl dodecane, 10-methyl dodecane, 11-methyl dodecane,), pentadecane or its derivatives (e.g., 3,7,11-trimethyl dodecane, 13-methyl tetradecane), hexadecane or its derivatives (e.g., 7-(methyl) pentadecane, 7-(3-propyl)tridecane), heptadecane or its derivatives (e.g., 11-methyl hexadecane, 14-methyl hexadecane, 2-methyl hexadecane), octadecane or its derivatives (e.g., 11-methyl heptadecane), nonadecane or its derivatives (e.g. 14-methyl octadecane) eicosane or its derivatives (e.g., 3,7,11,15-tetramethyl hexadecane, 9-(3-propyl)heptadecane), heneicosane or its derivatives (e.g., 20-methylheneicosane), docosane or its derivatives (e.g., 20-methyl heneicosane), tetracosane (e.g., 11-methyl tricosane), and a combination thereof, where the combination can include a polymer that includes two or more different hydrophobic side changes. In an embodiment, one or more of the hydrocarbon chains can be substituted. In an embodiment, at least one C—H bond in the position alpha to the ammonium group can be replaced by an electronegative group selected from the group consisting of F, Cl, and Br. Examples of hydrophobic side chain moieties are described in Example I. In an embodiment, the hydrophobic side chain moiety can include a C═C group in the chain (e.g., at the terminal end). In an embodiment, the hydrophobic side chain moiety can have an alkene group attached to it so that the carbon chain includes one or more C═C bonds.

In an embodiment, the photo cross-linkable moiety (e.g., B) functions to at least undergo a photochemical change to covalently bond with a surface or a layer on the surface of a structure having a C—H group. In an embodiment, the polymer composition is covalently bonded via the interaction of the polymer with a UV light (e.g., about 250 nm to 500 nm or about 340 to 370 nm) that causes a C—C bond to form between the polymer and the surface or a layer on the surface having the C—H group. The UV light can be generated from a UV light source such as those known in the art.

In an embodiment, the photo cross-linkable moiety can include an aryl ketone (about 340 to 400 nm), an aryl azide group (about 250 to 450 nm or about 350 to 375 nm), a diazirine group (about 340 to 375 nm), and the polymer can include a combination of these groups. In an embodiment, the photo cross-linkable moiety can include alkyl-arylketones and diarylketones bearing at least one condensed ring system substituent such as naphtyl and anthracenyl (See Example IV). In an embodiment, the aryl ketone group can include benzophenone (about 340 to 380 nm), acetophenone (about 340 to 400 nm), a naphthylmethylketone (about 320 to 380 nm), a dinaphthylketone (about 310 to 380 nm), a dinaphtylketone derivative (about 320 to 420 nm), or derivatives of each of these. In an embodiment, the photo cross-linkable moiety is a benzophenone group. In an embodiment, the aryl azide group can include phenyl azide, alkyl substituted phenyl azide, halogen substituted phenyl azide, or derivatives of each of these. In an embodiment, the diazirine group can include 3,3 dialkyl diazirine (e.g., 3,3 dimethyl diazirine, 3,3 diethyl diazirine), 3,3 diaryl diazirine (e.g., 3,3 diphenyl diazirine), 3-alkyl 3-aryl diazirine, (e.g., 3-methyl-3-phenyl diazirine), or derivatives of each of these. Additional examples are described in FIG. 1.4.

As mentioned above, the polymer can be disposed on a surface to produce a structure that includes the polymer covalently bonded (via a photochemical process) to the surface of the structure. In an embodiment, the method of disposing the polymer on the surface of the structure includes disposing the polymer on the surface using a method such as spraying, dipping, painting, spin coating, drop casting, and the like. In an embodiment, the surface of the structure has C—H groups that can interact (e.g., form C—C bonds) with the polymer upon exposure to UV light. In an embodiment, the structure has a layer (also referred to as a "functionalized layer") (e.g., a thin film or self assembling layer) disposed on the surface of the structure. The functionalized layer includes C—H bonds that can interact (form C—C bonds) with the polymer upon exposure to UV light. Additional details are described in the Examples. The structure can be exposed to UV light in many different ways such as direct exposure to a UV light source, exposure to UV light during the spray coating process, exposure to UV light during the dip coating process, exposure to UV light during the spincoating process, exposure to UV light during dip padding, exposure to UV light during nip padding, exposure to UV light during kiss rolling, and exposure to UV light during the drop-casting process.

Either during application of the polymer or once the polymer is disposed on the surface, UV light is directed onto the polymer on the surface. As described above, the UV light causes a photochemical reaction to occur between the polymer and the surface to form one or more covalent bonds (C—C bonds) between the polymer and the surface.

The wavelength of the UV light can be selected based on the photo cross-linkable moiety. In general, the UV light can be active to form the C—C bonds at about 190 to 500 nm, about 190 to 350, about 340 to 400 nm, or about 360 to 370 nm. The specific wavelength(s) that can be used for a particular photo cross-linkable moiety are described herein. In an embodiment, the UV light can be active to form the C—C bonds at a wavelength of about 340 to 370 nm. In an embodiment, the UV light can be active to form the C—C bonds at a wavelength of about 365 nm.

In an embodiment, after the polymer is covalently bonded to the surface, the structure may have an antimicrobial characteristic that is capable of killing a substantial portion of the microorganisms (e.g., bacteria) on the surface of the structure and/or inhibits or substantially inhibits the growth of the microorganisms on the surface of the structure. The phrase "killing a substantial portion" includes killing at least about 70%, at least about 80%, at least about 90%, at least about 95%, or at least about 99% of the microorganism (e.g., bacteria) on the surface that the polymer is covalently bonded, relative to structure that does not have the polymer disposed thereon. The phrase "substantially inhibits the growth" includes reducing the growth of the microorganism (e.g., bacteria) by at least about 70%, at least about 80%, at least about 90%, at least about 95%, or at least about 99% of the microorganisms on the surface that the polymer is covalently bonded, relative to a structure that does not have the polymer disposed thereon.

In an embodiment, once the structure has the polymer layer disposed on the entire surface or select portions of the surface, the structure can be exposed to the environment for which the structure is to be used. In an embodiment, the structure is used in the ocean, river, stream, collection pond, or lake. The structure can be introduced into the water and over a period of time the structure should have a smaller amount of microorganisms disposed on the structure relative to a structure without the polymer layer. Periodically, the structure can be exposed to the polymer material again to ensure that the previous polymer layer was not removed due to normal wear.

EXAMPLES

Example I:
Experimental Materials

Silicon wafers (UniversityWafer.com) with native oxide and glass slides (VWR) (cut into 3.8×2.5 cm pieces) were used as substrates. Poly(2-ethyl-2-oxazoline) (Aldrich), Cert-amylalcohol (Aldrich), 1-bromododecane (Alfa Aesar), iodomethane (Alfa Aesar), 4-hydroxybenzophenone (Alfa Aesar), 1,6 dibromohexane (Alfa Aesar), were used as received.

Instrumental Methods

AFM experiments were performed using a Multimode Nanoscope IIIa (Digital Instruments/Veeco Metrology Group). All measurements were performed using tapping mode. Null ellipsometry was performed on a Multiskop (Optrel GbR) with a 632.8 nm He—Ne laser beam as the light source. Both δ and ψ value thickness data were measured and calculated by integrated specialized software. At least three measurements were taken for every layer, and the average thickness was calculated.

Synthesis

Linear Polyethyleneimine (PEI):

The deacylation reaction was performed according to literature procedure (*PNAS*, 2005, 102, 5679). 3 g of the Poly(2-ethyl-2-oxazoline, $M_w$, 50 kDa) (POEZ) was added to 120 mL of 24% (wt/vol) HCl, followed by refluxing for 96 h. The POEZ crystal dissolved completely in 1 h, but after overnight reflux, a white precipitate appeared. The precipitate was filtered and then air-dried. The resultant protonated PEI was dissolved in water and neutralized with aqueous KOH to precipitate the polymer. The white powder was isolated by filtration, washed with distilled water until the pH of the washed liquid became neutral, and dried under vacuum. Yield: 1.15 g (88%). $^1$H NMR (CDCl$_3$): δ, 2.72 (s, 4H, NCH$_2$CH$_2$N), 1.71 (1H, NH).

Linear N,N-dodecyl methyl PEI:

The linear quaternized PEI was synthesized according to the literature procedure (*PNAS*, 2006, 103, 17667). 1 g (23.5 mmol of the monomer unit) of the PEI was dissolved in 12 mL of Pert-amyl alcohol, followed by the addition of 3.85 g (28.5 mmol) of K$_2$CO$_3$, and 16.5 mL (67 mmol) of 1-bromododecane, and the reaction mixture was stirred at 95° C. for 96 h. After removing the solids by filtration under reduced pressure, 2.8 mL of iodomethane was added, followed by string at 60° C. for 24 h in a sealed fluxed. The resultant solution was added to excess of ethylacetate; the precipitate formed was recovered by filtration under reduced pressure, washed with excess of ethylacetate and dried at room temperature under vacuum overnight. Yield: 3.2 g.

4-[(6-Bromohexyl)oxy]benzophenone

4-Hydroxy benzophenone (5.94 g, 30 mmol), 1,6 dibromohexane (8.05 g, 33 mmol), potassium carbonate (5.95 g, 45 mmol) and DMF (60 mL) were stirred at room temperature for 16 h under inert atmosphere. The reaction mixture was poured into ice water (300 mL) and extracted with ether (100 mL). The organic layer was collected and the solvent was removed by rotary evaporator. The crude product was purified on silica gel column by using 10:1 hexane ethylacetate mixture. Yield: 8.2 g (76%). $^1$H NMR (CDCl$_3$): δ, 7.81 (d, 2H, J=8.4 Hz), 7.75 (d, 2H, J=7.8 Hz), 7.54 (t, 1H, 7.5 Hz), 7.47 (t, 2H, J=6.9 Hz), 6.93 (d, 2H, J=9.0 Hz), 4.06 (t, 2H, J=6.3 Hz), 3.43 (t, 2H, 6.6 Hz), 1.86 (m, 4H), 1.50 (m, 4H). $^{13}$C NMR (CDCl$_3$): δ, 25.47, 28.10, 29.11, 32.86, 33.95, 68.2, 114.2, 128.37, 129.92, 129.94, 132.06, 132.78, 138.55, 162.9, 195.7.

1,6-Bis(4-benzoylphenoxy)hexane

4-Hydroxy benzophenone (5.94 g, 30 mmol), 1,6 dibromohexane (3.66 g, 15 mmol), sodium hydroxide (1.8 g, 45 mmol) and DMF (30 mL) were refluxed for 6 h under inert atmosphere. The reaction mixture was cooled at room temperature, poured into ice water (300 mL) and extracted with ether (100 mL). The organic layer was collected and the solvent was removed by rotary evaporator. The crude product was purified on silica gel column by using 10:1 hexane ethylacetate mixture. Finally compound was crystallized from DCM/hexane solvent mixture. Yield: 5.1 g (71%). $^1$H NMR (CDCl$_3$): δ, 7.82 (d, 4H, J=7.7 Hz), 7.75 (d, 4H, J=7.5 Hz), 7.56 (t, 2H, 7.2 Hz), 7.47 (t, 4H, J=7.2 Hz), 6.95 (d, 4H, J=9.0 Hz), 4.06 (m, 4H), 1.87 (br, 4H), 1.55 (br, 4H). $^{13}$C NMR (CDCl$_3$): δ, 26.06, 29.28, 43.52, 114.19, 114.22, 128.38, 129.90, 129.92, 132.06, 132.78, 138.72, 162.97.

Linear Copolymer of N,N-dodecyl methyl and N,N-[(6-hexyl)oxy]benzophenone methyl PEI:

0.5 g (12 mmol of the monomer unit) of the PEI was dissolved in 6 mL of tert-amyl alcohol, followed by the addition of 2.1 g (15 mmol) of K$_2$CO$_3$, 1.97 g (8 mmol) of 1-bromododecane, and 1.44 g of 4-[(6-bromohexyl)oxy]benzophenone and the reaction mixture was stirred at 95° C. for 96 h. After removing the solids by filtration under reduced pressure, 1.5 mL of iodomethane was added, followed by string at 60° C. for 24 h in a sealed fluxed. The solution was dried under rotary evaporator. The yellow solid was dissolve in minimum volume of dichloromethane and then added excess hexane to precipitate the polymer. Light yellow solid was filtered and dried at room temperature under vacuum for overnight. Yield: 2.3 g (46%). $^1$H NMR (CDCl$_3$): δ, 7.76 (bs, 4H); 7.56 (bs, 1H); 7.45 (bs, 2H); 6.98 (bs, 2H); 4.91-3.26 (m, 21H); 1.82 (bs, 6H); 1.65 (bs, 16H); 1.23 (bs, 34H), 0.66 (bs, 6H).

Preparation of Self-Assembled Monolayers (SAM) on Glass Substrates:

Glass slides were cut into rectangles. The substrates were sonicated with Fisherbrand sonicating soap, 18.2 MΩ deionized water, isopropanol, and acetone for 10 min each and finally dried in an oven for 1 h. After cleaning, a self-assembled monolayer of 7-octenyl trichlorosilane was formed from the vapor phase by suspending the substrates in a vacuum dessicator and placing two drops of silane on a glass substrate at the bottom. The substrates were kept in a vacuum flux constant pressure (100 millitorr) for 20 min. After venting with nitrogen, the substrates were sonicated with acetone and dried under air.

Surface Bound PEI Polymer (2a):

15 mg of quaternized PEI polymer and 10 mg of dibenzophenone was dissolved in 1 mL of chloroform solvent. The solution was filtered through 0.25 μm filter. The polymer film was developed on functionalized glass substrate by spin coating with 0.5 mL of solution at 1000 rpm. The glass substrate was radiated with UV light (360 nm, 180 mW/cm$^2$) for 15 minutes to covalently bound the polymer on glass surface with benzophenone as linker. The substrate was sonicated with acetone for one min and dried under air.

Surface Bound PEI Polymer (2b):

15 mg of quaternized polymer (2b) was dissolved in 1 mL of chloroform solvent. The solution was filtered through 0.25 μm filter. The polymer film was developed on functionalized glass substrate by spin coating with 0.5 mL of solution at 1000 rpm. The glass substrate was radiated with UV light (360 nm, 180 mW/cm$^2$) for 15 mins to covalently bound the polymer on glass surface with benzophenone as linker. The substrate was sonicated with acetone for one min and dried under air.

Scheme 2. Synthetic protocol for the hydrophobic PEI copolymer containing benzophenone moieties, 2b.

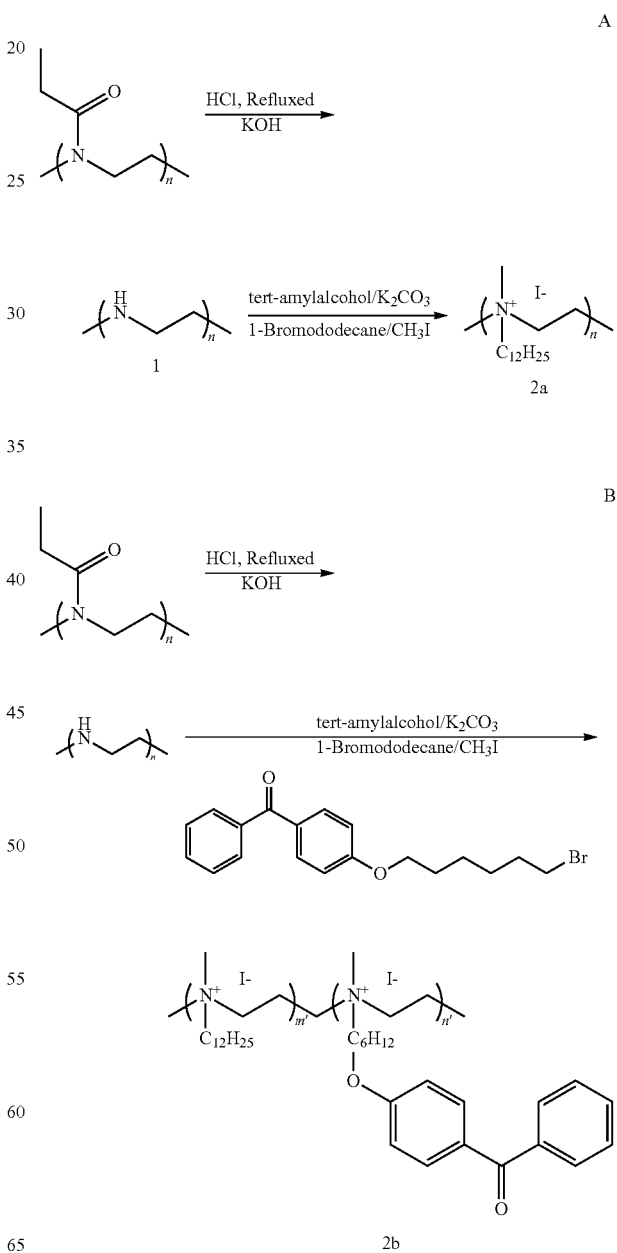

Scheme 3. Schematic showing the co-deposition of the dibenzophenone cross-linker along with hydrophobic PEI for covalent attachment.
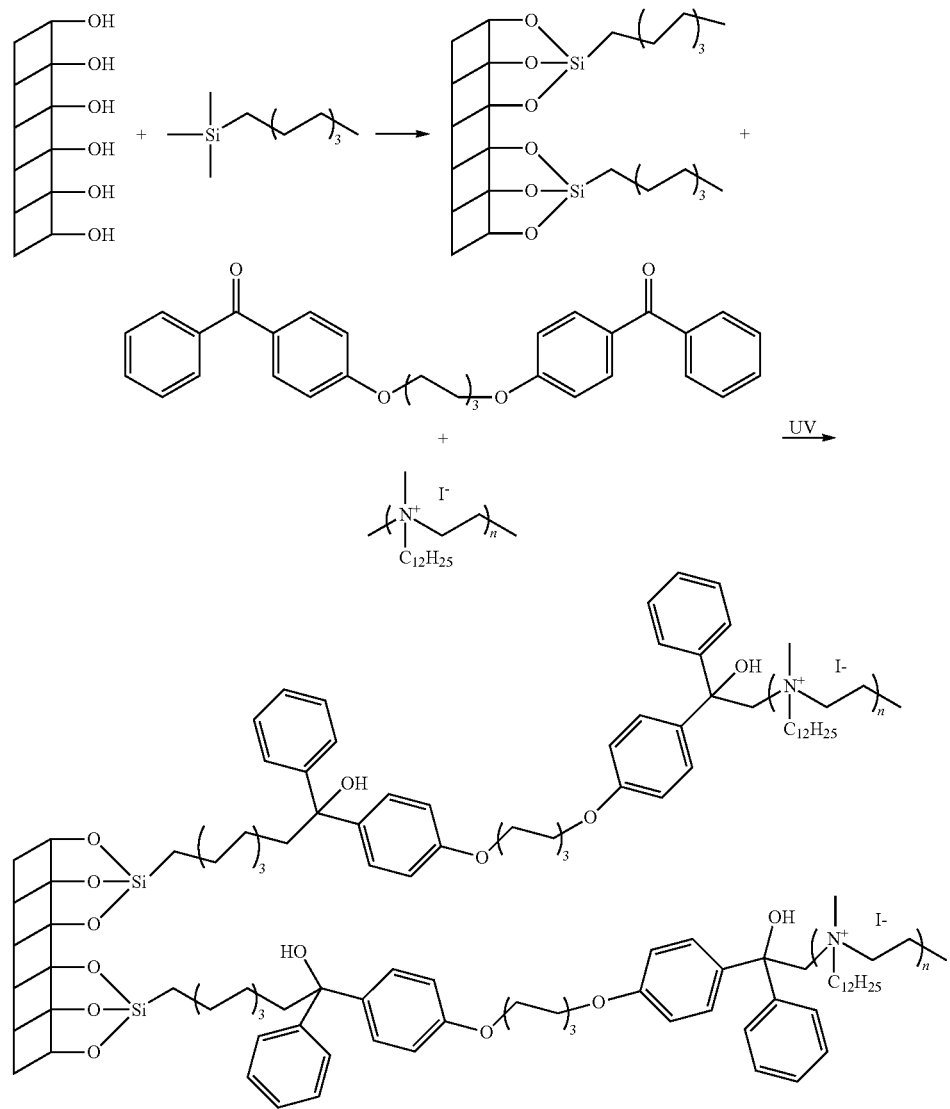
Scheme 4. Covalent attachment of the hydrophobic benzophenone-PEI copolymer directly to C—H bond using UV light.
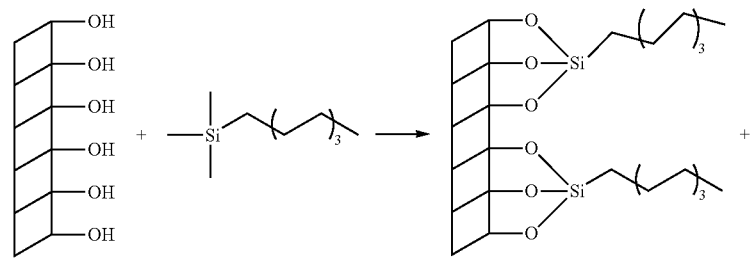

-continued

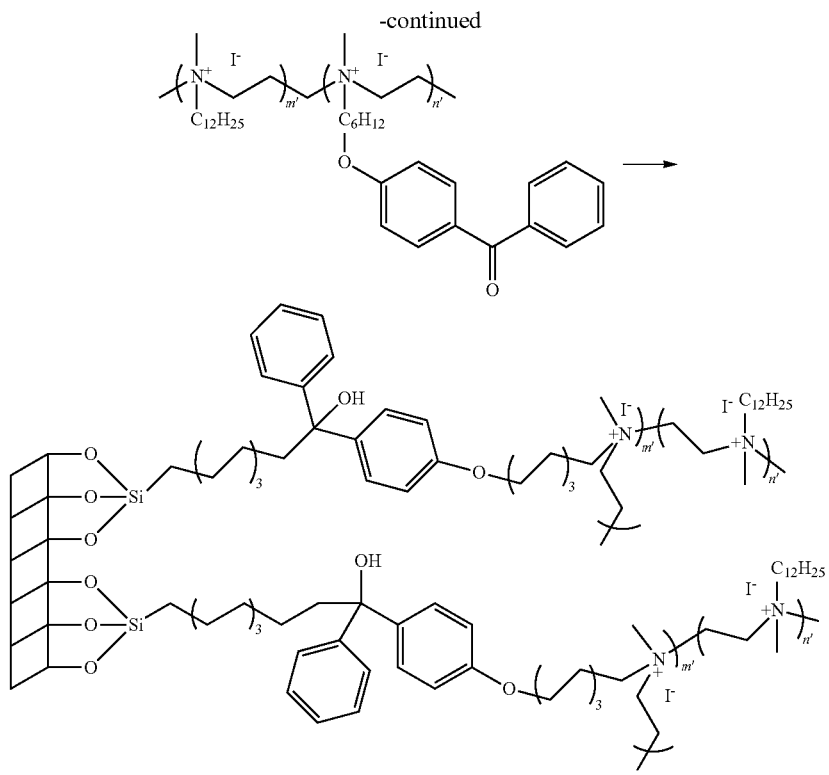

It will be recognized that the general process described in Scheme 4 can also be used to modify a silicate-based surface to render it with novel properties. For instance, if oligomers or polymers of, for instance, vinylfluoride ($-H_2C-CHF-)_x$, or tetrafluoroethylene ($-CF_2-CF_2-)_y$, are used instead of PEI, in a process similar to that in Scheme 4, a silicate surface could be rendered hydrophobic after undergoing covalent attachment of benzophenone-(fluorocarbon) copolymer.

Antimicrobial Test Method:

Trypticase Soy Broth (TSB) (10 ml) was inoculated with one loopful of *Staphylococcus aureus* culture and incubated overnight in a water shaker bath at 37° C. with 45 linear strokes per minute (TSB contains 17 g of casein peptone, 3 g of soy meal peptone, 2.5 g of D-(+) glucose, 5 g of NaCl and 2.5 g of dipotassium hydrogen phosphate per liter). 100 μl of an overnight *Staphylococcus aureus* culture was again inoculated with 10 ml of TSB and incubated for 4 hours in above mentioned conditions in the shaker bath. From freshly prepared 4 hour microbe culture 1 ml was transferred to 1.5 ml centrifuge tube. The tube was centrifuged at 5000 rpm for 1 minute at 21° C. (Centrifuge=accuSpin Micro 17R, Fisher Scientific, Tubes=Micro Centrifuge Tube, VWR International). The supernatant solution was discarded and fresh 1 ml of sterile water was added to the precipitated microbe tube. The microbes were re-suspended in the solution by using vortex mixer (Vortex Mixer=Vortex Genie 2). This re-suspended solution was transferred to 9 ml sterile water. The re-suspended solution was diluted ten times to get ~$3.4 \times 10^6$ colony forming units/ml (CFU/ml). Approximately 5 ml of this diluted solution was transferred to TLC sprayer bottle. The TLC sprayer bottle was connected to EFD (1500XL) pneumatic dispense regulator. The polymer coated substrates were uniformly sprayed in a controlled fashion from the TLC sprayer for 1 second at 30-40 psi pressure. The distance between the sprayer and glass slide was approximately 1-1½ feet. The sprayed sample was air dried for approximately 2 minutes and carefully mounted a sprayed surface of the sample on a Difco™ Trypticase Soy Agar (TSA) plate (TSA contains 15.0 g of pancreatic digest of casein, 5.0 g of enzymatic digest of soybean meal, 5.0 g of sodium chloride, and 15.0 g of agar per liter). TSA plates were incubated for 24 hours at 37° C. Finally the number of colonies grown on the slide was observed.

Launder-o-Meter Testing:

Approximately 1 sq inch of net samples was used for testing. The net sample was coated with 15 mg/ml of polymer 2b dissolved in acetone. The dissolved polymer solution was applied through spray coating and dabbing polymer solution soaked sponge on the both sides of net samples. Uncoated sample was used as control. Three replications were done for coated sample. Each sample was treated with 150 ml of 35 gpl (gram/liter) saline solution (NaCl) along with 50 steel balls (6 mm in diameter). The treatment was given in a closed stainless steel canister (500 ml, 75×125 mm) on an Atlas Launder-o-meter (AATCC standard instrument) at 49° C. for 45 minutes. The samples were rinsed with water and were tested for antibacterial efficacy.

Result and Discussions

Two quaternary amine polymer have been synthesized (2a and 2b) (FIG. 1.1) with (2b) and without (2a) attachment of a benzophenone moiety. Polymer 2a was synthesized according to the literature procedure (*Proceedings of the National Academy of Science* 2006, 103, 17667-17671, which is incorporated by reference). Another polymer 2b was prepared by reacting PEI polymer with 4-[(6-Bromohexyl)oxy]benzophenone and 1-bromododecane. The copolymer composition was checked by NMR spectroscopy, which revealed that the polymer composition matched the monomer feed ratio. Polymer 2a is soluble in halogenated solvents but insoluble in alcohols, where as polymer 2b is soluble in halogenated solvents and slightly soluble in alcohols. Polymer 2b is also readily soluble in acetone. Our strategy is to photochemically attach the polymer material onto the surface by using the benzophenone (BP) moiety as a cross-linker. Benzophenone is an ideal candidate for cross-linking because it is (1) useful for any organic surface or surface functionalized with an organic molecule which has a C—H bond; (2) it can be activated using very mild UV light (~345-360 nm), avoiding oxidative damage to the polymer and substrate by exposure to shorter wavelengths. (3) Benzophenone is chemically more stable than other organic crosslinkers and reacts preferentially with C—H bonds in a wide range of different chemical environments. Triggered by UV light, benzophenone has an n-π* transition, resulting in the formation of a biradical triplet excited state that then abstracts a hydrogen atom from neighboring aliphatic C—H group to form a new C—C bond.

While this mechanism provides the ability to coat any type of polymeric surface, we have used glass surfaces and silicon wafers to do the preliminary biocidal experiments because of the ease of surface analytical quantification. These substrates allow us to measure coating thickness and to observe changes in surface morphology upon irradiation with UV light. The substrates are coated with a self-assembled monolayer of organic silane to provide reactive C—H groups that will mimic plastic functionalization, while retaining very low roughness for accurate measurements of thickness. Fabrication of covalently bound polymer surfaces is shown in Scheme 3 and 4. In both cases, glass or silicon surfaces were functionalized with octyltrichlorosilane to generate C—H groups on the surface. This can be done with any trichloro-, trimethoxy-, or triethoxy-alkylsilane derivative. To this modified surface a thin layer of polymer 2a with dibenzophenone (Scheme 3) or polymer 2b was applied using a spin coater. This was to ensure smooth coating and a uniform film thickness. In the last step, the desired covalently attached films were generated by crosslinking through the benzophenone group with UV irradiation. To remove unbound materials, films were washed with acetone or sonicated in acetone for one minute. The thicknesses were measured for polymer film 2b before and after sonication and were 122 and 65 nm respectively. It is important to note that the polymers will covalently attach to any organic substrates with a C—H bond (examples are cotton, polyethylene, polypropylene, or other common plastics). In these cases, the covalently attached polymer surface can be generated without any functionalization because of the presence of C—H group on the surface.

The kinetics of surface attachment of the PEI copolymers with different irradiation times was investigated by UV-vis spectroscopy. Changes in the absorption spectra of the polymer film with 2b under UV light irradiation are shown in FIG. 1.1. Focusing on the BP photophore, absorption of a photon at 350 nm results in the promotion of one electron from a nonbonding $sp^2$ to an antibonding π*-orbital of the carbonyl group. In the diradicaloid triplet state, the electron-deficient oxygen n-orbital is electrophilic and therefore interacts with weak C—H δ-bonds, resulting in hydrogen (H) abstraction to complete the half-filled n-orbital. To confirm the photochemical attachment, we investigated the absorption spectroscopy with UV irradiation time. The π-π* absorption of benzophenone at 290 nm decreases with increasing irradiation time, indicating the decomposition of carbonyl group through the above photochemical reaction.

Atomic force microscopy (AFM) was use to characterized the surface morphology of polymer (2b) film before and after sonication to remove any non-covalently bound polymer from the surface. Before sonication, the polymer film was very smooth. A representative morphology for the film before sonication is shown by FIG. 1.2, which has an RMS roughness 0.48 nm. This is approximately the roughness of the glass substrate (0.39 nm) before functionalization. FIG. 1.3 shows the AFM image of the film after sonication. Though the basic morphology of surfaces are same before and after sonication, the roughness (0.83 nm) has slightly increased with sonication due to the removal of any non-covalently attached polymer from the surface. The AFM measurements, along with the thickness values measured with ellipsometry confirm the attachment of the polymer to the substrate surface.

The ability of the polymer-coated surfaces to kill bacteria was tested for different textile woven and non-woven fabrics and glass substrates. The density of the quaternized amine polymer played an important role in the biocidal activity (Table 1). We examined the surfaces with a coating varying from 10 to 65 nm in thickness. The surface grafted with a high density of polymers exhibited relatively high biocidal activity. When the thickness of the polymer layer is greater than 50 nm, essentially all the bacteria are killed. FIG. 1.4 shows the digital photograph of the control and polymer functionalized surfaces incubated with bacteria. As seen in FIG. 1.4a, numerous colonies of S. aureus grown on the control slide after spraying the bacterial suspension onto its surface. On the other hand no colonies were found on the polymer functionalized surface (FIG. 1.4b).

TABLE 1

There were four sets of samples tested: 1. Control Glass, 2. Spin coated glass slide with 5 mg/ml polymer concentration, 3. Spin coated glass slide with 10 gm/ml polymer, and Spin coated glass slide with 15 mg/ml concentration. The different concentrations allow control over different thickness values. The copolymer (2b) was spin coated on the glass sample and UV irradiated with 360 nm light of an intensity 180 mW/cm$^2$ and then sonicated for 1 minute. The coated and control samples were sprayed with S. aureus solution. TMTC ~ too many to count.

| Rep. | Control glass | 5 mg/ml Polymer coated Glass (22 nm) | 10 mg/ml Polymer coated Glass (50 nm) | 15 mg/ml polymer coated glass (65 nm) |
|---|---|---|---|---|
| 1 | TMTC | 30 | 15 | 0 |
| 2 | TMTC | 42 | 18 | 0 |
| 3 | TMTC | 29 | 12 | 0 |

TABLE 2

There were four sets tested 1. Control cotton sample, 2. Polymer spray coated cotton sample without UV radiation, 3. Polymer spray coated cotton sample with UV radiation, and 4. Polymer spray coated cotton sample with UV radiation and acetone washed. Microbe Tested: Staphylococcus aureus (gram positive bacteria). Digital images are shown in FIG. 1.5.

| Rep. | Control Cotton | No UV radiation (Polymer conc. 15 mg/ml) | UV radiation & No wash (Polymer conc. 15 gm/ml) | Acetone washed (Polymer conc. 15 gm/ml) |
|---|---|---|---|---|
| 1 | TMTC | 10 | 0 | 7 |
| 2 | ~150 | 6 | 5 | 0 |
| 3 | ~300 | 0 | 8 | 1 |
| Average | 225 | 8 | 6.5 | 4 |
| % Reduction | — | 96.44 | 97.11 | 98.22 |

TABLE 3

There were two sets tested with *Escherichia coli* (gram negative bacteria) 1. Control glass slide and 2. Glass substrate with 65 nm thick polymer 2b.

| Rep. | Control Glass | Substrate |
|---|---|---|
| 1 | ~280 | 0 |
| 2 | TMTC | 0 |
| 3 | ~100 | 0 |
| Average | 190 | 0 |
| % Reduction | — | 100 |

TABLE 4

There were three sets tested: 1. Control polypropylene substrate (Ten Cate Nicolon geosynthetic product), 2. Polymer spray coated and UV irradiated sample and 3. Polymer spray coated, UV irradiated and acetone washed sample. Microbe Tested: *Staphylococcus. aureus* (gram positive bacteria). Digital pictures are shown in FIG. 1.6.

| Rep. | Control | UV radiated | UV radiated Acetone washed |
|---|---|---|---|
| 1 | TMTC | 6 | 31 |
| 2 | TMTC | 7 | — |
| 3 | TMTC | 12 | — |

Launder-o-meter testing: The durability of coating was analyzed through launder-o-meter test. There were three different sets of substrates used namely, (1) PVC coated net samples as a control, (2) PVC net coated samples coated with polymer 2b and UV radiated and (3) PVC net coated samples coated with polymer 2b and UV radiated and laundered using above mentioned procedure. The laundered sample showed less microbial growth compared to control samples. The number of colonies on samples was not countable. The digital pictures are shown in FIG. 1.7.

Example II

Testing in aquatic environments: The effectiveness of the polymer coating on polyvinylchloride substrates was tested by submerging 1 m² of the substrates shown in FIG. 1.7 in the southern (off the Chilean coast) and northern (off the Canadian coast) hemispheres to account for seasonal variations in aquaculture environments. The substrates were examined after 30 and 60 days of testing. The substrates that were coated with polymer 2b were effective at preventing bacteria adsorption on the polymer substrates. After 30 days, the uncoated samples were completely covered with bacteria, algae, barnacles, and other sea creatures, while the substrates coated with polymer 2b were free of fouling, except for a thin film of dead bacteria. After 60 days, the 2b coated substrates had succumbed to bacterial adsorption because of biofouling on the dead bacteria surface. This coating of bacteria and algae was easily wiped away, while the fouled, uncoated substrates, were very difficult to clean by hand, and required excessive pressure washing with a stream of high pressure water.

Example III

Additional polymer structures to add vinyl functional groups to the surface using photocrosslinking polymers.

Linear Copolymer of N,N-undecene methyl and N,N-[(6-hexyl)oxy]benzophenone methyl PEI:

0.25 g (6 mmol of the monomer unit) of the PEI was dissolved in 6 mL of tert-amyl alcohol, followed by the addition of 1 g (7 mmol) of $K_2CO_3$, 1.17 g (5 mmol) of 11-bromo-1-undecene, and 0.36 g of 4-[(6-bromohexyl)oxy]benzophenone and the reaction mixture was stirred at 95° C. for 96 h. After removing the solids by filtration under reduced pressure, 1 mL of iodomethane was added, followed by string at 60° C. for 24 h in a sealed fluxed. The solution was dried under rotary evaporator. The yellow solid was dissolve in minimum volume of dichloromethane and then added excess hexane to precipitate the polymer. Light yellow solid was filtered and dried at room temperature under vacuum for overnight. Yield: 1 g (44%).

Functionalization of PEI Polymer on Other Polymer Surface:

15 mg of quaternized polymer was dissolved in 1 mL of acetone solvent. The solution was filtered through 0.25 μm filter. The polymer film was developed on Hytrel-4056 or Petrothene polymer surface by spin coating with 0.5 mL of solution at 1000 rpm. The polymers were radiated with UV light (360 nm, 180 mW/cm²) for 30 mins to covalently bound the PEI copolymer on other polymer surfaces with benzophenone as linker. The substrate was sonicated with acetone (for Hytrel-4056) or acetone/methanol (30:70) mixture (for Petrothene) for one minute and dried under air.

Scheme 5. Synthetic scheme for PEI copolymer containing vinyl functionality.

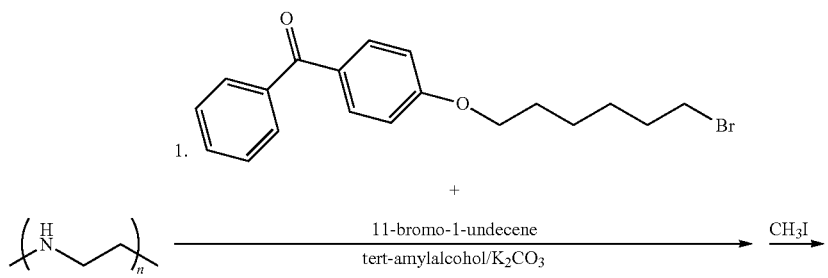

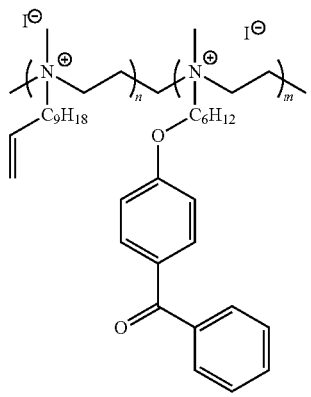

Result and Discussions:

We have synthesized quaternary amine polymer with a attachment of benzophenone moiety. The polymer was prepared by reacting PEI polymer with 4-[(6-Bromohexyl)oxy]benzophenone and 11-bromo-1-undecene. The polymer was characterized by both NMR and IR to confirmed the presence of benzophenone and undecene moieties. The polymer is soluble in halogenated solvents and acetone and slightly soluble in methanol or ethanol. Our strategy is to photochemically attach the polymer material onto the surface using the benzophenone (BP) moiety as a cross-linker, as described herein.

In the present example we use two different polymer surfaces, Hytrel-4056 and Petrothene for surface coating purposes. Hytrel-4056 is a polyester and petrothene is a linear polyethylene. The surface attachment of the PEI copolymer was investigated by FTIR. FIG. 2.1 shows the FTIR spectra of Hytrel-4056, PEI functionalized Hytrel-4056, and the spectrum for the PEI copolymer. FTIR clearly indicates that the coated Hytrel sample (bottom graph, FIG. 2.1) has all characteristic peaks for Hytrel polymer as well as PEI copolymer except for the C=O absorbance peak at 1735 cm$^{-1}$, which is from the benzophenone unit in the PEI copolymer. The disappearance of this peak upon crosslinking indicates covalent attachment between the two polymers. Also the coated sample has a weak absorption peak at 3078 cm$^{-1}$ corresponding to C=C—H stretching mode, which is an indication that the vinyl functionality is retained in the sample after crosslinking.

FIG. 2.2 shows the IR spectra of PEI copolymer, Petrothene coated with PEI copolymer and Petrothene. The Petrothene sample (bottom) has no significant absorption between 1600 cm$^{-1}$ to 1000 cm$^{-1}$ where as PEI polymer coated petrothene (middle) show several absorptions due to the PEI containing copolymer in this region. IR data confirmed the covalent attachment of PEI copolymer onto the petrothene surface through the disappearance of the C=O stretching peak at 1735 cm$^{-1}$ as indicated above.

Example IV

The attachment of functionalized diaryl(or alkylaryl) ketones to surfaces can be achieved using active C—H bonds in the substrate (to undergo insertion of the keto group), and the selection of the appropriate wavelength of the UV incident radiation such as to promote homolysis of the keto group π bond. Consequently, myriad surfaces are potentially suitable to undergo irreversible attachment of functionalized ketones, which in turn will enable the development of multiple surface modifications and coatings of industrial importance.

In an embodiment, materials having the either of the following chemical structures can be used to attached to one or more surfaces.

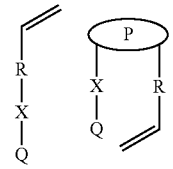

Q is a photo cross-linkable moiety such as those described above in reference to B. In an embodiment, Q can be attached to two "X—R-vinyl group" groups, where the "X—R-vinyl group" are the same or different. X can include C, O, N, B, S, Al, Si, P, or Sn, where one or more additional moieties (e.g., a second vinyl group (e.g., R-vinyl group), H, an alkyl group, and the like (e.g., X can be CH$_2$)) can be attached to X as needed (e.g., to satisfy atom's normal valence). R can include a substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl, combinations of each, and the like. Semicircle P can include a polymer, compound, and the like, where multiple photo cross-linkable moiety and/or vinyl groups can be included.

In an alternative embodiment, the —(HC=CH$_2$) terminal group connected to R, can actually be other groups, such as substituted alkenes such as in acrylic acid fragment (CH$_2$CH$_2$CO(OH)), esters of acrylic acid (e.g., methyl acrylate that would lead to PMMA attached to the first surface), amine or diamine (which could lead to polyamide or such as nylon, or aramid by reaction with lactams or diacyl and diamine), alcohol/diol/polyols (e.g., —CH(OH)—CH$_2$—CH(OH)—CH(OH)—CH$_3$), which can lead to polyesters through reaction with diacids and diols) and diacids (e.g., HOC(O)—CH$_2$—CH$_2$—C(O)OH).

In an embodiment, the material can include either of the following chemical structures can be used to attached to one or more surfaces.

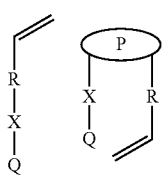

In addition, three exemplar types of materials (A through C shown below in Example IV) that can be used to modify the properties of Hytrel and poly(ethylene) [used herein as model substrates] that will provide terminal double bonds to the surface of the polymers for further grafting are herein described. These modifications will be applied to commercial items made of PE and/or Hytrel, along with any other necessary polymers for surface grafting, for further modification of the tethered units. In this example, "vinyl" may refer to the —CHCH$_2$ moiety connected through an alkyl spacer (and or a heteroatom) to an aromatic ketone.

A. Small Molecule Synthesis of Vinyl Benzophenone Materials that can be Directly Grafted Using Mild UV Light.

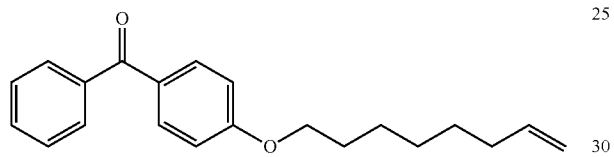

Example 1

Monosubstituted, Alkoxy-Linked Benzophenone Containing a Linear —OC$_6$H$_{12}$ Spacer Between the Vinyl Functionality and the Benzophenone Moiety Above is the structure of the benzophenone used as model for surface modification for the addition of tethered HC═CH$_2$ functionality onto a surface. The alkyl spacer linker between terminal vinyl group and BP can be varied between C6-C18. Surface characterization of the functionalized polymers can be performed using attenuated total reflection spectroscopy and surface force/tension measurements. The above substituted benzophenone can be reacted with the surface of a first polymer substrate (e.g., PMMA), in the presence of UV light, to yield a modified first surface containing multiple covalently bound —O—C(H)(C$_6$H$_5$) (C$_6$H$_4$—C$_6$H$_{12}$—CH═CH$_2$) moieties, in which the tethered vinyl groups can then be either polymerized, blended, and crosslinked through radical or cross-metathesis chemistry or other carbon-carbon bond forming reactions, to yield a polymer cross-linked by covalent C—C bonds.

The above substituted benzophenone can be reacted with the surface of a first polymer substrate (e.g., PMMA), in the presence of UV light, to yield a modified first surface containing multiple covalently bound —O—C(H)(C$_6$H$_5$) (C$_6$H$_4$—C$_6$H$_{12}$—CH═CH$_2$) moieties, in which the tethered vinyl groups can then be polymerized (e.g., directly or through reaction with ethylene) to yield a first polymer surface coated by a covalently bound monolayer of PE (See FIG. 5.1). This yields a first surface (e.g., PMMA) modified by a monolayer of a second surface (e.g., PE) in which the first and second surfaces are covalently bound to each other by diphenylmethoxy groups.

B. Polymer Backbone Modification.

Polymethacrylates with different compositions of vinyl monomers and BP side chains can be copolymerized for further grafting of polymers. The benzophenone moiety is used to conduct the light-promoted attachment to a first surface, while tethered vinyl group is used for further grafting of a polymer (that constitutes the second surface) bound to the first surface (x and y are independently about 1 to 50 or 1 to 20). These monomers can be copolymerized by both radical, controlled radical, and other polymerization methodologies.

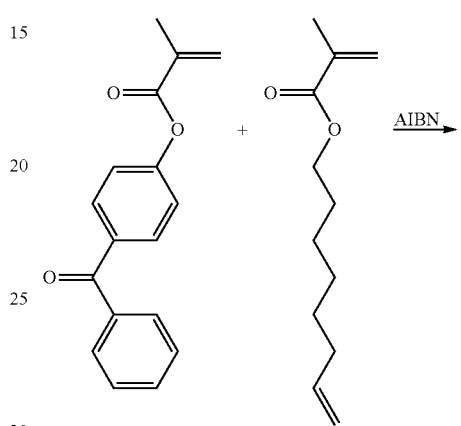

C. Silicone Backbone Modification

Hydrosilization reactions can be used to generate surface attachable siloxanes used to modify silicone backbones. Further grafting to yield the second surface or crosslinking can be done through the same method as described in B.

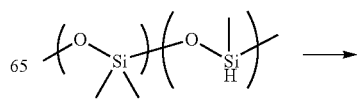

-continued

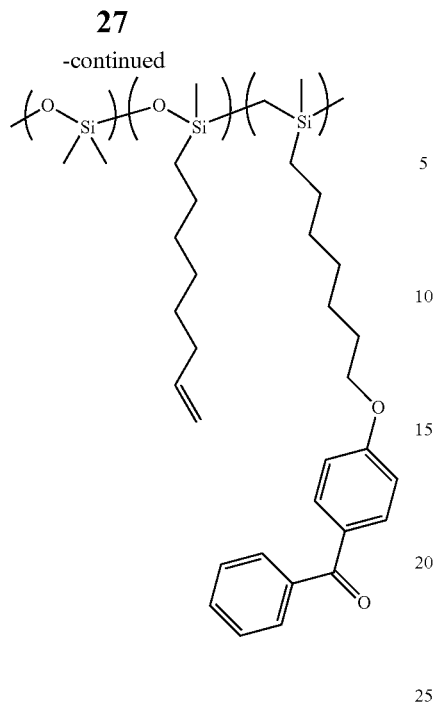

It will be recognized that in addition to the aromatic ketones of A through C, other variants of such ketones may be employed, under similar conditions, to yield similar results. Examples of ketones that may be used in the reaction schemes under A-C, and in place of the ketones described therein are described in Examples 2-5 below. Such ketones would provide a framework for a three-dimensional second surface comprised of, for instance, cross-linked PE. Additionally, thioketones (RR'C=S) are also capable of providing a way of attachment of a second surface onto a first surface, by the methods described herein.

It will also be recognized that the linkage of the [alkyl spacer-vinyl] unit (R') to the aromatic ketone group may be accomplished through means other than through C, O, N, illustrated in examples 1-5. For instance, and without intending to be limiting, —SR', —SnR'$_3$, [Fe(Cp-R')$_2$]$^+$, NR'$_3^+$, cyclic —C$_6$H$_6$R'$_6$, may be used to link multiple R' units to a single ketone group.

It will be further recognized that the embodiments of the present disclosure are not limited to the use of benzophenone. Alkyl-arylketones, as well as diarylketones bearing at least one condensed ring system substituent such as naphtyl and anthracenyl, may also be employed and their attachment to the original surface may be promoted by simple choice of a UV radiation of suitable wavelength.

Example 2

Monosubstituted Benzophenone Bearing Multiple Vinyl Groups [1≤n≤18]

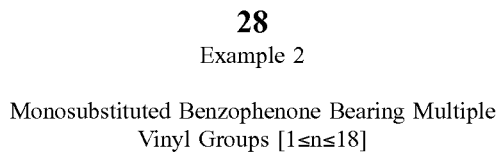

Example 3

Disubstituted Benzophenone Bearing Multiple Vinyl Groups [1≤n≤18]

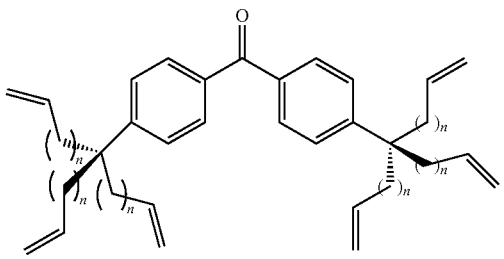

Example 4

Mono(divinylamino)-Substituted Benzophenone Bearing Multiple Vinyl Groups [1≤n≤18]

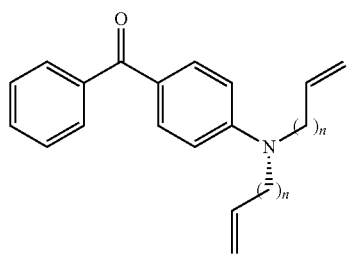

Example 5

Bis(divinylamino)-Substituted Benzophenone Bearing Multiple Vinyl Groups [1≤n≤18]

Example 5 is a prototypical example of heteroatom linkage to the aromatic ketone. It is further recognized that C, O, B, S, Al, Si, P, Sn, may replace N to yield novel benzophenone structures and that highly derivatized, organic (e.g., pentaallyl-substituted cyclohexyl) and organometallic frag-

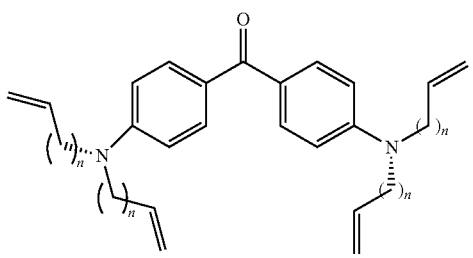

ments (e.g., allyl-substituted ferrocenyl, vinyl-substituted chromocene and metallo-carbonyl derivatives) may also be linked to the aromatic ketone moiety. It is noted that these substitutions can alter the wavelength of light needed to excite the radical coupling reaction.

It will further be recognized that the embodiments of the present disclosure are not limited to the attachment of a PE-based second surface to an original surface or crosslinking reactions. Through the appropriate choice of a terminus for the tethered group, such terminus being a monomer of a polymer or a monomer for a copolymer, the second surface or cross-linking matrix may be comprised of different polymers. For instance, an acrylate group to yield a polyacrylate second surface or cross-linked matrix; an organic diacid to yield a polyester-based second surface or cross-linked matrix through reaction with a diol; a diacylchloride to yield a polyamide (or aramid)-based second surface or cross-linked matrix through reaction with an appropriate diamine; trifluorovinyl to yield a poly-trifluoroethylene second surface; an alkyne terminus to yield a polyacetylene-based second surface.

Such modifications can lead to modifications of properties of articles of polymers constituents of the first surface. For instance, articles made of a mechanically strong, but hydrophilic, material may be made hydrophobic by the modification herein, through the appropriate design of a tethered group that can be used for grafting of a hydrophobic polymer.

The substrate (first surface) can be any surface with C—H bonds that are reactive through the process described herein. Examples include, without limitation, materials such as keratin, polyethylene, cellulose, acrylics, pectin, lignin, chitin, PVC, among others, as well as others described herein.

Example V

Brief Introduction:

Antimicrobial copolymers of hydrophobic N-alkyl and benzophenone containing polyethylenimines were synthesized from commercially available linear poly(2-ethyl-2-oxazoline), and covalently attached to surfaces of synthetic polymers, cotton, and modified silicon oxide using mild photocrosslinking. Specifically, these polymers were applied to polypropylene, poly(vinyl chloride), polyethylene, cotton, and alkyl coated oxide surfaces using solution casting or spray coating and then covalently crosslinked rendering permanent, nonleaching antimicrobial surfaces. The photochemical grafting of pendant benzophenones allows immobilization to any surface that contains a C—H bond. Incubating the modified materials with either *Staphylococcus aureus* or *Escherichia coli* demonstrated that the modified surfaces had substantial antimicrobial capacity against both Gram-positive and Gram-negative bacteria (>98% microbial death).

Introduction:

Microbial infection is one of the most serious concerns for many commercial applications such as textiles, food packaging and storage, shoe industry, water purification, medical devices, and dental surgery equipment.[1-4] Recently, antimicrobial agents have gained significant interest from both an academic and industrial point of view because of their potential to provide safety benefits to a diverse range of materials. Some cationic polymers, like quaternary polyetheleneimines (QPEIs), have proven effective at killing bacteria because of their unique structural and hydrophobic properties.[5-10] The generally accepted hypothesis for antimicrobial activity of polycations with hydrophobic side chains is that the pendant hydrophobic groups can intercalate into the hydrophobic portion of a cell membrane, while the electrostatic interaction of the positively charged backbone and the negatively charged bacterial cell membrane/wall disrupts the ionic integrity of the membrane, causing cell death.[11-15] However, a more detailed mechanism for rapid contact kill of bacteria at the solid surface interface remains an important unexplored research area. To achieve this goal, the development of a new methodology for surface immobilization of antimicrobial polymers with well-defined properties is necessary. It is also of great interest to obtain biocidal effects without releasing biocide material into the environment, which means that antimicrobial coatings need to be immobilized irreversibly or covalently attached to surfaces. A significant number of literature reports discuss the preparation of antimicrobial surfaces via the covalent coupling of poly quaternary ammonium (PQA) compounds to a variety of surfaces like glass,[16-18] polymer,[19-25] paper,[26] and metal.[27] Recently, Hsu and Klibanov[28] reported a system in which an aryl azide based biocidal PEI copolymer was used to modify cotton fabrics. In this case, the nitrophenylazide based crosslinker reacts preferentially with the hydroxy functionality on the cellulose surface. While this methodology is achievable with surfaces that contain reactive functional groups (examples include hydroxy, amine, carboxylic acid, and chloro), the covalent attachment of biocidal polymers on common and inert plastic surfaces such as polyethylene, polypropylene, and polystyrene is more challenging with very few examples in the literature.[29-32]

The ability of benzophenone (BP) to act as a cross-linking agent and abstract hydrogen from a suitable hydrogen donor has been well studied and utilized in various chemical systems for many years.[33-39] BP is an ideal choice for crosslinking organic thin films, because it can be activated using mild UV light (345-365 nm), avoiding oxidative damage of the polymer and substrate that can occur upon exposure to higher energy UV. The benzophenone moiety is more chemically robust than other organic crosslinkers and reacts preferentially with C—H bonds in a wide range of different chemical environments. Triggered by UV light, benzophenone undergoes an $n-\pi^*$ transition, resulting in the formation of a biradical triplet excited state that can abstract a hydrogen atom from a neighboring aliphatic C—H group to form a new C—C bond.[40] This photoreaction has recently been used to attach thin polymer layers to metal and oxide surfaces,[41-46] along with applications in microfluidics,[47] organic semiconductors,[48] redox polymers,[49,50] and biosensors.[51]

In this article we describe a convenient method to covalently attach ultrathin biocidal polymer coatings on surfaces with inert functionality. We have synthesized antimicrobial copolymers with pendant benzophenone groups that act as a photo-crosslinker for the covalent attachment of the polymer with any substrate containing a C—H bond upon irradiation with UV light. The coated substrates showed impressive antibacterial and antifouling properties. To our knowledge, this is the first demonstration for the covalent immobilization of antimicrobial polymers onto inert polymer surfaces.

Experimental:

Materials:

Silicon wafers (Universitywafer.com) with native oxide and glass slides (VWR) (cut into 2.5×2.5 cm pieces) were used as substrates. Poly(2-ethyl-2-oxazoline) (Aldrich), tert-amylalcohol (Aldrich), 1-bromododecane (Alfa Aesar), iodomethane (Alfa Aesar), 4-hydroxybenzophenone (Alfa Aesar), 1,6-dibromohexane (Alfa Aesar), trypticase soy broth (TSB) (Difco), trypticase soy agar (TSA) (Difco), were used as received.

Instrumental Methods:

Atomic force microscopy (AFM) experiments for quaternized PEI based polymer films were performed using a Multimode Nanoscope IIIa (Digital Instruments/Veeco Metrology Group). All measurements were performed using tapping mode. Null ellipsometry was performed on a Multiskop (Optrel GbR) with a 632.8 nm He—Ne laser beam as the light source. Both δ and ψ values were measured and thickness was calculated by integrated specialized software. At least three measurements were taken for every layer, and the average thickness was calculated. UV-vis spectroscopy was performed on a Cary 50 spectrophotometer (Varian). Infrared spectroscopy studies of polymer coated films were done using a Thermo-Nicolet Model 6700 spectrometer equipped with a variable angle grazing angle attenuated total reflection (GATR-ATR) accessory (Harrick Scientific). The UV light source was an OmniCure, Series 1000 with 365 nm bandpass filter, equipped with a liquid filled fiber optic waveguide. The substrates were held 2 cm from the source and irradiated with a power of 180 mW/cm$^2$.

Antibacterial Test Method:

Trypticase soy broth (TSB) (10 ml) was inoculated with one loopful of bacteria Staphylococcus aureus (ATCC 6538) culture or Escherichia coli (ATCC 25922) and incubated overnight in a water shaker bath at 37° C. with 45 linear strokes per minute (TSB contains 17 g of casein peptone, 3 g of soy meal peptone, 2.5 g of D-(+) glucose, 5 g of NaCl and 2.5 g of dipotassium hydrogen phosphate per liter). The new TSB (10 ml) was again inoculated with 100 µl of an overnight bacterial culture and incubated for 4 hours in the above-mentioned conditions in the shaker bath. One milliliter of this culture was transferred to a 1.5 mL centrifuge tube and was centrifuged at 5000 rpm for 1 minute at 21° C. to precipitate bacteria and form a bacterial pellet. (Centrifuge=accuSpin Micro 17R, Fisher Scientific, Tubes=Micro Centrifuge Tube, VWR International). The supernatant solution was discarded and 1 mL of sterile water was added to the microbial pellet in the tube. The microbes were re-suspended in the solution by using a vortex mixer (Vortex Genie 2) and was transferred to 9 mL of sterile water to make a bacterial concentration of ~3×10$^6$ cfu (colony forming units) and subsequently transferred to thin layer chromatography (TLC) sprayer bottle which was connected to pneumatic dispense regulator (EFD 1500XL). The polymer coated substrates were uniformly sprayed on one side in a controlled fashion from the TLC sprayer for 1 second at 30-40 psi pressure. The distance between the sprayer and glass slide was approximately 1-1½ feet. The sprayed sample was air dried for approximately 1 minute and the sample was carefully mounted on a Difco™ Trypticase soy agar (TSA) plate (TSA contains 15.0 g of pancreatic digest of casein, 5.0 g of enzymatic digest of soybean meal, 5.0 g of sodium chloride, and 15.0 g of agar per liter). TSA plates were incubated for 24 hours at 37° C. Finally, the number of colonies grown on the slide was counted.

Synthesis

Linear Polyethylenimine (PEI):

The deacylation reaction was performed according to literature procedures.[52] 3 g of poly(2-ethyl-2-oxazoline, $M_w$, 50 kDa) (POEZ) was added to 120 mL of 24% (wt/vol) HCl, followed by refluxing for 96 h. The POEZ dissolved completely in 1 h, but after overnight reflux a white precipitate appeared. The precipitate was filtered and then air-dried. The resultant protonated, linear PEI was dissolved in water and neutralized with aqueous KOH to precipitate the polymer. The white powder was isolated by filtration, washed with distilled water until the pH became neutral, and dried under vacuum. Yield: 1.15 g (88%). $^1$H NMR (CDCl$_3$): δ, 2.72 (s, 4H, NCH$_2$CH$_2$N), 1.71 (1H, NH).

4-[(6-Bromohexyl)oxy]benzophenone

4-Hydroxy benzophenone (5.94 g, 30 mmol), 1,6 dibromohexane (8.05 g, 33 mmol), potassium carbonate (5.95 g, 45 mmol) and DMF (60 mL) were stirred at room temperature for 16 h under inert atmosphere. The reaction mixture was poured into ice water (300 mL) and extracted with ether (100 mL). The organic layer was collected and the solvent was removed with a rotary evaporator. The crude product was purified on a silica gel column by using 10:1 hexane: ethyl acetate mixture. Yield: 8.2 g (76%). $^1$H NMR (CDCl$_3$): δ, 7.81 (d, 2H, J=8.4 Hz), 7.75 (d, 2H, J=7.8 Hz), 7.54 (t, 1H, 7.5 Hz), 7.47 (t, 2H, J=6.9 Hz), 6.93 (d, 2H, J=9.0 Hz), 4.06 (t, 2H, J=6.3 Hz), 3.43 (t, 2H, 6.6 Hz), 1.86 (m, 4H), 1.50 (m, 4H). $^{13}$C NMR (CDCl$_3$): δ, 25.47, 28.10, 29.11, 32.86, 33.95, 68.2, 114.2, 128.37, 129.92, 129.94, 132.06, 132.78, 138.55, 162.9, 195.7.

Linear Copolymer of N,N-dodecyl methyl and N,N-[(6-hexyl)oxy]benzophenone methyl PEI:

0.5 g (12 mmol of the monomer unit) of the PEI was dissolved in 6 mL of tert-amyl alcohol, followed by the addition of 2.1 g (15 mmol) of K$_2$CO$_3$, 1.99 g (8 mmol) of 1-bromododecane, and 1.44 g (4 mmol) of 4-[(6-bromohexyl)oxy]benzophenone and the reaction mixture was stirred at 95° C. for 96 h. After removing the solids by filtration under reduced pressure, 1.5 mL of iodomethane was added, followed by stirring at 60° C. for 24 h in a sealed, heavy walled pressure vessel. After reaction, the solution was dried using a rotary evaporator. The yellow solid was dissolved in a minimum volume of dichloromethane and then the solution was added to excess hexane to precipitate the polymer. The light yellow solid was filtered and dried at room temperature under vacuum for 12 hours. Yield: 2.3 g (46%). $^1$H NMR (CDCl$_3$): δ, 7.77 (bs, 4H); 7.56 (bs, 1H), 7.45 (bs, 2H); 6.96 (bs, 2H); 4.19-3.26 (m, 21H); 1.83 (bs, 6H); 1.65 (bs, 16H); 1.23 (bs, 34H), 0.87 (bs, 6H). $^{13}$C NMR (CDCl$_3$): δ, 195.73, 162.88, 138.24, 132.56, 131.72, 129.71, 128.25, 114.32, 67.95, bs 53.45, 31.90, 29.65, 29.59, 29.53, 29.47, 29.36, 22.67, 14.11.

Preparation of Self-Assembled Monolayers on Glass Substrates:

Glass slides were cut into rectangles. The substrates were sonicated with Fisherbrand sonicating soap, 18.2 MΩ deionized water, isopropanol, and acetone for 10 min each and finally dried in an oven for 1 h. After cleaning, a self-assembled monolayer (SAM) of octyltrichlorosilane was formed from the vapor phase by suspending the substrates in a vacuum desiccator and placing two drops of silane on a glass substrate at the bottom. The substrates were kept in a vacuum flux (constant pressure of 100 millitorr) for 20 min. After venting with nitrogen, the substrates were sonicated with acetone and dried under air.

Surface Bound PEI Polymer (2):

15 mg of quaternized polymer (2) was dissolved in 1 mL of acetone solvent. The solution was filtered through 0.25 µm filter. The polymer film was developed on functionalized glass substrate by spin coating with 0.5 mL of solution at 1000 rpm. The glass substrate was irradiated with UV light (365 nm, 180 mW/cm$^2$) for 15 mins to covalently bind the polymer on the glass surface through the pendant benzophenone moiety. The substrate was sonicated with acetone for one minute and dried under air.

Scheme 6. Outline of the synthetic protocol for the PEI copolymer containing benzophenone sidechains.

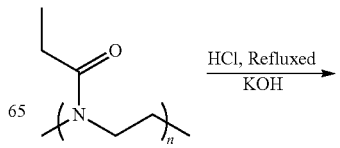

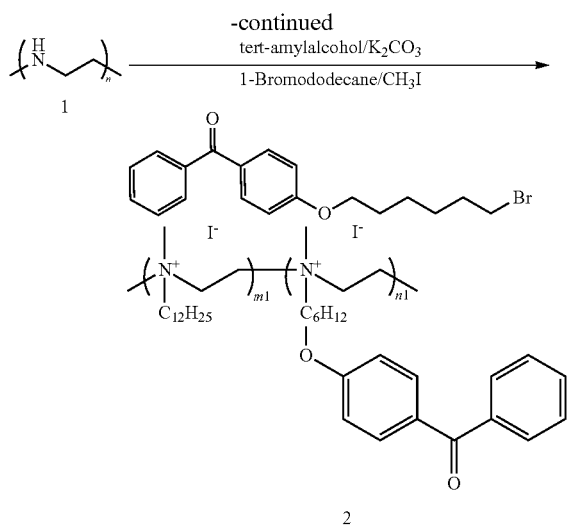

Result and Discussions:

Copolymer 2, which contains both hydrophobic and benzophenone side chains, was prepared by reacting linear PEI with 4-[(6-Bromohexyloxy)]benzophenone and 1-bromododecane (Scheme 1) along with subsequent quaternization using iodomethane. The copolymer composition was checked by NMR spectroscopy, which revealed that the polymer composition matched the pendant group feed ratio. Copolymer 2 is soluble in halogenated solvents, acetone, and slightly soluble in alcohols. As described above, the benzophenone component of 2 can act as a cross-linker between the hydrophobic PEI polymer and any organic substrate through C—H activation. Initially, we have used glass and silicon wafers functionalized with alkyl SAMs to analyze the polymer film thickness before and after cross-linking, kinetics of functionalization, and to observe any surface morphology changes through atomic force microscopy. Flat substrates also simplify the antimicrobial activity assays because of the ease of analytical quantification.

Scheme 7. Covalent attachment of the hydrophobic benzophenone-PEI copolymer to alkyl-containing surfaces.

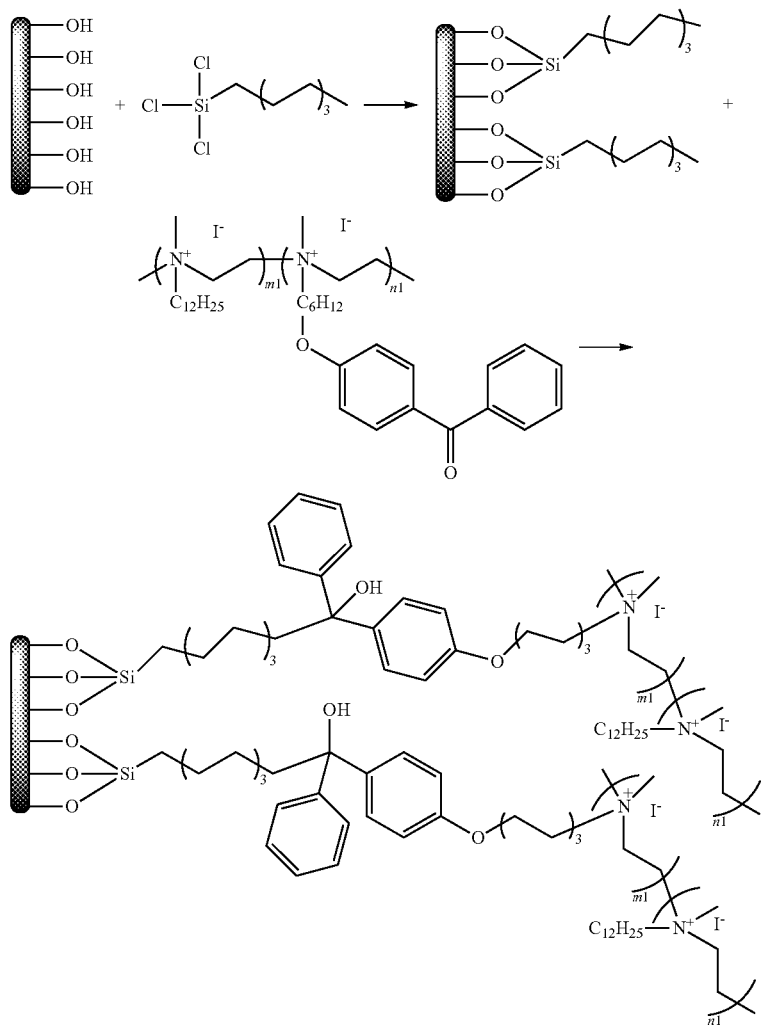

The cross-linking and structure of the covalently bound polymer surfaces is shown in Scheme 7 (other types of polymer of the present disclosure can be used in place of the one shown in Scheme 7). Initially, the oxide surfaces were functionalized with octyltrichlorosilane (OTS) to generate C—H alkyl groups on the surface. To this modified surface a thin layer of polymer 2 was deposited using spin coating (15 mg/mL in acetone, 1000 rpm). Covalent attachment was generated by exposure to UV irradiation (365 nm, 180 mW/cm$^2$) for 15 minutes. The crosslinked films were then washed with acetone and sonicated in acetone for one minute to remove any residual, unbound materials. The polymer film thickness was measured before and after sonication and was observed to be 93 and 77 nm respectively, indicating that approximately 80% of the coating remained after cross-linking. The thickness of the cross-linked coating did not change upon prolonged sonication in any organic solvent.

The kinetics of surface attachment of copolymer 2 was investigated by UV-vis spectroscopy on OTS functionalized quartz substrates. Time dependent changes in the absorption spectra of the film under UV light irradiation are shown in FIG. 1.1.[53] Photon absorption at 365 nm results in the promotion of one electron from a nonbonding n-orbital to an antibonding π*-orbital of the carbonyl group on the benzophenone moiety. The n-π* transition yields a biradicaloid triplet state where the electron-deficient oxygen n-orbital is electrophilic and therefore interacts with weak C—H δ-bonds, resulting in hydrogen abstraction to complete the half-filled n-orbital.[54,55] The two resulting radical species can then combine to form a new C—C bond. The reaction progress can be monitored indirectly by following the decrease in the π-π* transition of benzophenone at 290 nm. As expected, this peak decreases with increasing irradiation time. After ~30 minutes, the reaction is complete as observed, with no further changes in the spectrum with prolonged irradiation.

The photochemical attachment of copolymer 2 was also confirmed using grazing incidence attenuated total internal reflection fourier transform infrared spectroscopy (GATR-FTIR). Copolymer 2 was spincast onto a silicon wafer that was modified with a SAM of OTS. FIG. 3.1 shows the GATR-IR spectrum of a silicon wafer modified with copolymer 2 (A) before and (B) after UV irradiation. In FIG. 3.1, spectra A, the peaks at 2920 and 2849 cm$^{-1}$ are due to C—H stretching of the aliphatic backbone and pendant groups. The C═O of the benzophenone pendant group is observed at 1648 cm$^{-1}$. The C—C ring vibrations are assigned at 1600 cm$^{-1}$ along with the C—N$^+$ stretch at 1468 cm$^{-1}$. Peaks at 1253 and 1020 cm$^{-1}$ are assigned to the C—O—C asymmetric and symmetric stretches respectively. FIG. 3.1, spectra B shows the polymer film after irradiation. A significant reduction in the C═O stretch at 1648 cm$^{-1}$ is readily apparent, which indicates photo-decomposition of the carbonyl group along with the covalent attachment of 2 onto the OTS functionalized SiO$_2$ surface. The overall decrease in all peak intensities correlates with the decrease in film thickness after crosslinking and subsequent sonication.

AFM was used to characterize the surface morphology of copolymer (2) film before and after sonication to remove any non-covalently bound polymer from the surface. Before and after sonication, the irradiated film of 2 was very smooth. A representative morphology for both is shown in FIGS. 1.2 and 1.3. The thickness of the film is 93 nm (measured with ellipsometry) with an RMS roughness 0.48 nm by AFM. FIG. 1.3 shows the morphology of the film after sonication. The overall film thickness decreased to 77 nm after sonication, with an increase in surface roughness to 0.83 nm due to removal of non-covalently attached polymer from the surface.

The effectiveness of the polymer-coated surfaces to kill bacteria was tested on different plastics, fabrics and alkyl functionalized glass substrates. For covalently bonded biocides, direct contact of the organism with the antimicrobial moiety is required for the antibacterial activity.[56,57] In these experiments, microbes were uniformly sprayed on the polymer coated surfaces using a TLC sprayer connected to pneumatic dispense regulator. The sprayed sample was air dried and mounted on a TSA plate which was incubated for 24 hours at 37° C. The number of colonies grown on the slide was then counted by visualization under an optical microscope. To examine the influence of polymer coating thickness on the biocidal activity, copolymer 2 was spin-cast onto flat substrates using solutions of different concentration. This allowed uniform, reproducible thickness that varied between 30-93 nm after irradiation and sonication. The thickness of the coating had an impact on the biocidal activity (Table 1). The surface grafted with a high density of polymers exhibited relatively high biocidal activity. When the thickness of the polymer layer is greater than 50 nm, the coating was >99% effective and all bacterial colonies were killed. FIG. 3.2 shows the digital photograph of the control and polymer functionalized surfaces after spraying with *S. aureus* and incubated for 24 hours at 37° C. As seen in FIG. 3.2A, numerous colonies of *S. aureus* are grown on the control slide after spraying the bacterial suspension onto the surface. On the other hand, a bacterial reduction greater than 99% is observed on the same substrate coated with copolymer 2 (FIG. 3.2B).

TABLE 1

Example V. Antimicrobial test with S. aureus along with percent bacterial reduction. There were four sets of samples tested: (1) Control glass substrate with OTS coated SAM, (2) spin coated glass substrate with 5 mg/mL polymer concentration, (3) spin coated glass substrate with 10 mg/mL polymer, and (4) spin coated glass substrate with 15 mg/mL concentration. The copolymer (2) was spin coated on the glass sample and irradiated with UV light (365 nm, 180 mW/cm$^2$) for 15 minutes and sonicated in acetone for 1 minute. The coated and control samples were sprayed with S. aureus solution and incubated for 24 hours at 37° C.

|  | Control | 5 mg/ml polymer conc. | | 10 mg/ml polymer conc. | | 15 mg/ml polymer conc. | |
| --- | --- | --- | --- | --- | --- | --- | --- |
|  | (CFU) Uncoated glass slides | SUV* Film Thickness 35 nm | SUVS* Film Thickness 31 nm | SUV Film Thickness 55 nm | SUVS Film Thickness 53 nm | SUV Film Thickness 93 nm | SUVS Film Thickness 77 nm |
| 1 | 258 | 1 | 15 | 0 | 3 | 0 | 4 |
| 2 | 247 | 4 | 16 | 0 | 4 | 0 | 2 |
| 3 | 158 | 0 | 10 | 0 | 3 | 3 | 2 |
| Average | 221 | 1.66 | 13.66 | 0 | 3.33 | 1 | 2.66 |
| % Reduction | — | 99.24 | 93.81 | 100 | 98.49 | 99.54 | 98.79 |

*SUV = Spin-coated UV radiated unsonicated glass slides
*SUNS = Spin-coated UV radiated sonicated glass slides

TABLE 2

Example 5. Antimicrobial test with E. coli along with percent bacterial reduction. There were four sets of samples tested: (1) Control glass substrate with OTS coated SAM, (2) spin coated glass substrate with 5 mg/mL polymer concentration, (3) spin coated glass substrate with 10 mg/mL polymer, and (4) spin coated glass substrate with 15 mg/mL concentration. The copolymer (2) was spin coated on the glass sample and irradiated with UV light (365 nm, 180 mW/cm$^2$) for 15 minutes and sonicated in acetone for 1 minute. The coated and control samples were sprayed with S. aureus solution and incubated for 24 hours at 37° C.

|  | Control | 5 mg/ml polymer conc. | | 10 mg/ml polymer conc. | | 15 mg/ml polymer conc. | |
| --- | --- | --- | --- | --- | --- | --- | --- |
|  | (CFU) Uncoated glass slides | SUV* Film Thickness 35 nm | SUVS* Film Thickness 31 nm | SUV Film Thickness 55 nm | SUVS Film Thickness 53 nm | SUV Film Thickness 93 nm | SUVS Film Thickness 77 nm |
| 1 | 91 | 0 | 11 | 1 | 0 | 0 | 1 |
| 2 | 81 | 2 | 24 | 0 | 11 | 0 | 0 |
| 3 | 136 | 2 | 26 | 0 | 6 | 0 | 1 |
| Average | 102.66 | 1.33 | 20.33 | 0.33 | 5.66 | 0 | 0.66 |
| % Reduction | — | 98.70 | 80.19 | 99.67 | 94.48 | 100 | 99.35 |

*SUV = Spin-coated UV radiated unsonicated glass slides
*SUVS = Spin-coated UV radiated sonicated glass slides To establish the generality of the effectiveness of our polymer coatings, we also tested against the human pathogenic bacterium *Escherichia coli* (*E. coli*, which is a Gram-negative bacterium). The results of which are shown in Table 2. As also seen in FIG. 3.3, the polymer-coated slides once again afforded a 99% killing efficiency against *E. coli*.

In order to investigate the versatility of these copolymers on commodity plastics and textile fabrics, variety of substrates such as cotton, polypropylene, polyethylene and poly(vinyl chloride) were photochemically modified with copolymer 2 using simple spray coating technique. The copolymer, dissolved in acetone, was uniformly sprayed coated with a laboratory TLC sprayer. The substrates were air dried and irradiated (365 nm, 180 mW/cm$^2$) to covalently attach the polymer to the plastic surface. After UV curing, the substrates were thoroughly washed in acetone to remove any non-covalently attached copolymer. The copolymer treated and untreated fabrics were challenged against *S. aureus* with the antibacterial test method described earlier. FIG. 3.4 shows bacterial proliferation on the untreated fabrics and excellent antibacterial activity on the treated fabrics. The results demonstrate covalent immobilization of polymer 2 on all substrates, including those with reactive functional groups such as cotton as well as on inert plastic surfaces such as polypropylene, poly(vinyl chloride) and polyethylene.

Conclusions:

In this Example, we have demonstrated a novel and efficient approach to covalently attach antimicrobial polymer on any substrate with a C—H bond. A hydrophobic PEI copolymer substituted with benzophenone side chain (2) was spin-casted or spray-coated on a wide range of surfaces from cotton to inert plastics and photo-crosslinked by UV irradiation. After the covalent attachment of polymer on the surface, the biocidal activity was investigated against both Gram-positive (*S. aureus*) and Gram-negative (*E. coli*) bacteria. The surface grafted with a high density of polymers exhibited relatively high biocidal activity. When the thickness of the polymer layer was greater than 50 nm, essentially almost all the bacteria were killed. This one step photochemical attachment process of an ultrathin antimicrobial coating is both simple and scalable for industrial applications.

References, each of which is incorporated herein by reference:

(1) Kenawy, E.-R.; Worley, S. D.; Broughton, R. *Biomacromolecules* 2007, 8, 1359.
(2) Patel, M. B.; Patel, S. A.; Ray, A.; Patel, R. M. *J. Appl. Poly. Sci.* 2003, 89, 895.
(3) Ferreira, L.; Zumbuehl, A. *J. Mater. Chem.* 2009, 9, 7796.
(4) Gabriel, G. J.; Som, A.; Madkour, A. E.; Eren, T.; Tew, G. N. *Mat. Sci. Eng. R* 2007, 57, 28.
(5) Klibanov, A. M. *J. Mater. Chem.* 2007 17 2479.
(6) Yudovin-Farber, I.; Golenser, J.; Beyth, N.; Weiss, E. I.; Domb, A. J. *J. Nanomater.* 2010, 2010, 1.
(7) Yudovin-Farber, I.; Beyth, N.; Nyska, A.; Weiss, E. I.; Golenser, J.; Domb, A. J. *Biomacromolecules* 2008, 9, 3044.
(8) Koplin, S. A.; Lin, S.; Domanski, T. *Biotechnol. Prog.* 2008, 24, 1160
(9) Beyth, N.; Houri-Haddad, Y.; Baraness-Hadar, L.; Yudovin-Farber, I.; Domb, A. J.; Weiss, E. I. *Biomaterials* 2008, 29, 4157.
(10) Gao, B.; Zhang, X.; Zhu, Y. *J. Biomat. Sci.-Polym. E.* 2007, 18, 531.
(11) Tiller, J. C.; Liao, C.-J.; Lewis, K.; Klibanov, A. M. *P. Natl. Acad. Sci. USA* 2001, 98, 5981.
(12) Grapski, J. A.; Cooper, S. L. *Biomaterials* 2001, 22, 2239.
(13) Lee, S. B.; Koepsel, R. R.; Morley, S. W.; Matyjaszewski, K.; Sun, Y.; Russell, A. J. *Biomacromolecules* 2004, 5, 877.
(14) Lin, J.; Qiu, S.; Lewis, K.; Klibanov, A. M. *Biotechnol. Prog.* 2002, 18, 1082.
(15) Milović, N. M.; Wang, J.; Lewis, K.; Klibanov, A. M. *Biotechnol. Bioeng.* 2005, 90, 715.
(16) Madkour, A. E.; Dabkowski, J. M.; Nusslein, K.; Tew, G. N. *Langmuir* 2009, 25, 1060.
(17) Murata, H.; Koepsel, R. R.; Matyjaszewski, K.; Rusell, A. J. *Biomaterials* 2007, 28, 4870.
(18) Lee, S. B.; Koepsel, R. R.; Morley, S. W.; Matyjaszewski, K.; Sun, Y.; Russell, A. J. *Biomacromolecules* 2004, 5 877.
(19) Cen, L.; Neoh, K. G.; Kang, E. T. *Langmuir* 2003, 19, 10295.
(20) Cheng, Z.; Zhu, X.; Shi, Z. L.; Neoh, K. G.; Kang, E. T. *Ind. Eng. Chem.* 2005, 44, 7098.
(21) Hu, F. X.; Neoh, K. G.; Cen, L.; Kang, E. T. *Biotechnol. Bioeng.* 2005, 89, 474.
(22) Lin, J.; Murthy, S. K.; Olsen, B. D.; Gleason, K. K.; Klibanov, A. M. *Biotechnol. Lett.* 2003, 25, 1661.
(23) Lin, J.; Qiu, S.; Lewis, K.; Klibanov, A. M. *Biotechnol. Bioeng.* 2003, 83, 168.
(24) Lin, J.; Tiller, J. C.; Lee, S. B.; Lewis, K.; Klibanov, A. M. *Biotechnol. Lett.* 2002, 24, 801.
(25) Tiller, J. C.; Lee, S. B.; Lewis, K.; Klibanov, A. M. *Biotechnol. Bioeng.* 2002, 79, 465.
(26) Jampala, S. N.; Sarmadi, M.; Somers, E. B.; Wong, A. C. L.; Denes, F. S. *Langmuir* 2008, 24, 8583.
(27) Ignatova, M.; Voccia, S.; Gilbert, B.; Markova, N.; Mercuri, P. S.; Galleni, M.; Sciannamea, V.; Lenoir, S.; Cossement, D.; Gouttebaron, R.; Jérôme, R.; Jérôme, C. *Langmuir* 2004, 20, 10718.
(28) Hsu, B. B.; Klibanov, A. M. *Biomacromolecules* 2011, 12, 6.
(29) Huang, J.; Murata, H.; Koepsel, R. R.; Russell, A. J.; Matyjaszewski, K. *Biomacromolecules* 2007, 8, 1396.
(30) Steven, M. D.; Hotchkiss, J. H. *J. Appl. Poly. Sci.* 2008, 110, 2665.
(31) Bilyk, A.; Li, S.; Murphy, J.; Petinakis, S.; Zeerdin, K.; Scully, A. *Prog. Org. Coat.* 2008, 62, 40.
(32) Goddard, J. M.; Hotchkiss, J. H. *Prog. Polym. Sci.* 2007, 32, 698.
(33) Turro, N. J. *Modern molecular photochemistry*; Benjamin/Cummings Pub. Co.: Menlo Park, Calif., 1978.
(34) Lin, A. A.; Sastri, V. R.; Tesoro, G.; Reiser, A.; Eachus, R. *Macromolecules* 1988, 21, 1165.
(35) McCaig, M. S.; Paul, D. R. *Polymer* 1999, 40, 7209.
(36) Oster, G.; Oster, G. K.; Moroson, H. *J. Polym. Sci.* 1959, 671.
(37) Lin, A. A.; Sastri, V. R.; Tesoro, G.; Reiser, A.; Eachus, R. *Macromolecules* 1988, 21, 1165.
(38) Brauchle, C.; Burland, D. M.; Bjorklund, G. C. *J. Phys. Chem.* 1981, 85, 123.
(39) Higuchi, H.; Yamashita, T.; Horie, K.; Mita, I. *Chem. Mater.* 1991, 3, 188.
(40) Turro, N. J. *Modern Molecular Photochemistry*; University Science Books: Mill Valley, Calif., 1991.
(41) Prucker, O.; Naumann, C.; Rühe, J.; Knoll, W.; Frank, C. W. *J. Am. Chem. Soc.* 1999, 121 8766.
(42) Pahnke, J.; Rühe, J. *Macromol. Rapid Comm.* 2004, 25, 1396.
(43) Leshem, B.; Sarfati, G.; Novoa, A.; Breslav, I.; Marks, R. S. *Luminescence* 2004, 19, 69.
(44) Toomey, R.; Freidank, D.; Rühe, J. *Macromolecules* 2004, 37, 882.
(45) Naumann, C. A.; Prucker, O.; Lehmann, T.; Rühe, J.; Knoll, W.; Frank, C. W. *Biomacromolecules* 2002, 3, 27.
(46) Shen, W. W.; Boxer, S. G.; Knoll, W.; Frank, C. W. *Biomacromolecules* 2001, 2, 70.
(47) Jeyaprakash, J. D.; Samuel, S.; Brenner, T.; Prucker, O.; Grumann, M.; Ducree, J.; Zengerle, R.; Rühe, J. *Macromol. Chem. Physic* 2010, 211, 195.
(48) Virkar, A.; Ling, M.-M.; Locklin, J.; Bao, Z. *Synthetic Met.* 2008, 158, 958.
(49) Bunte, C.; Prucker, O.; Küonig, T.; Rühe, J. *Langmuir* 2010, 26, 6019.
(50) Bunte, C.; Rühe, J. *Macromol. Rapid Comm.* 2009, 30, 1817.
(51) Brandstettera, T.; Böhmer, S.; Prucker, O.; Bissé, E.; Hausen, A. z.; Alt-Mörbe, J.; Rühe, J. *J. Viral. Methods* 2010, 163 40.
(52) Thomas, M.; Lu, J. J.; Ge, Q.; Zhang, C.; Chen, J.; Klibanov, A. M. *P. Natl. Acad. Sci. USA* 2005, 102, 5679.
(53) Park, M.-K.; Deng, S.; Advincula, R. C. *J. Am. Chem. Soc.* 2004, 126, 13723.
(54) Dorman, G.; Prestwich, G. D. *Biochemistry* 1994, 33, 5661.
(55) Horie, K.; Ando, H.; Mita, I. *Macromolecules* 1987, 20, 54.
(56) Worley, S. D.; Sun, G. *Trends Polym. Sci.* 1996, 4, 364.
(57) Ho, C. H.; Tobis, J.; Sprich, C.; Thomann, R.; Tiller, J. C. *Adv. Mater.* 2004, 16, 957.

Example VI
Experimental

Materials: Ethylene-methyl acrylate copolymer (Optema TC 115), low density polyethylene (LDPE) (SABIC 2100), ethyl vinyl acetate (EVA) (Elvax® 460), 4-hydroxybenzophenone (TCI), 11-bromo-1-undecene (Sigma-Aldrich) were used as received.

Instrumentation:

The coated substrates were dissolved in deuterated benzene for proton NMR analysis and spectra were recorded using a Varian Mercury 500 NMR spectrometer working at 500 MHz. An internal standard of tetramethylsilane was used to report relative chemical shifts.

Synthesis:

The reaction mixture of 4-hydroxybenzophenone (0.99 g, 5 mmole), 11-bromo-1-undecene (1.16 g, 5 mmole), $K_2CO_3$ and n,n-dimethylformamide (DMF) (20 ml) was stirred at room temperature for 16 hours under inert atmosphere. The reaction mixture was poured into ice water (100 ml) and extracted with ether (3×20 ml). The organic layer was collected, and the solvent was removed by rotary evaporator. The crude product was purified on silica gel column by using 10:1 hexane/ethyl acetate mixture. $^1$H NMR 300 MHz, ($CDCl_3$): δ, 7.81 (d, 2H, J=6.3 Hz), 7.76 (d, 2H, J=7.2 Hz), 7.56 (d, 1H, J=7.3 Hz), 7.46 (t, 2H, J=8.7 Hz), 6.94 (d, 2H, J=8.4 Hz), 5.88 (m, 1H), 4.91 (m, 2H), 4.04 (t, 2H, J=7.7 Hz), 2.2 (q, 2H), 1.81 (p, 2H), 1.31 (m, 12H).

Scheme 1 of Example VI: Synthesis of modified benzophenone (BP1): phenyl(4-(undec-10-enyloxy)phenyl)methanone

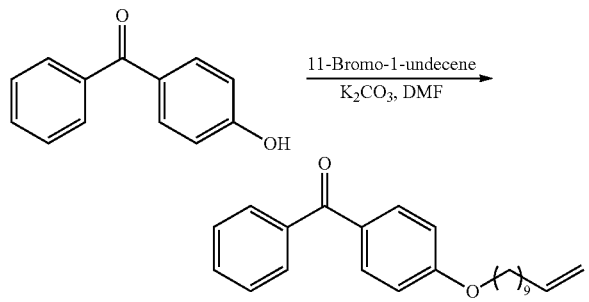

Coating Procedure:

The polymer substrates (provided in powder form ground from pellets) were coated with BP1 using different concentrations of coating solutions. The modified BP was dissolved in acetone and spray/slurry coated on the substrates. Upon air drying, the substrates were irradiated with mild UV to attach the coating onto the substrate surface. The coating to substrate ratio was varied from 33:100 to 5:100. The coated substrate was washed with acetone to remove any non-bonded, physisorbed BP1 material.

FIGS. 4.1 and 4.2 shows the proton NMR spectra of copolymer coated with different concentration of BP1. Both the spectra clearly showed surface modification of given copolymer. Aromatic protons (7.47, 7.37, 6.32 ppm), vinyl protons (5.4 and 4.62 ppm) and protons from ether linkage (3.16 ppm) of coating were observed. The given ethylene-methyl acrylate copolymer contains 12% methyl acrylate polymer component. The amount of modified benzophenone coating was calculated based on the assumption of 12% acrylate content. The peak integration calculations showed that in the case of coating and copolymer ratio of 33:100, there was approximately 6.52% coating (based on ether linkage of BP1) and 5.12% coating (based on the aromatic protons from BP1) was left on the surface (FIG. 4.1). In the case of coating and copolymer ratio of 5:100, there was approximately 1.56% coating (based on ether linkage of BP1) and 0.96% coating (based on the aromatic protons from BP1) was left on the surface (FIG. 4.2) after rinsing away physisorbed materials.

The coating procedure was repeated on other polymers with a different chemical nature. The polymers namely, low density polyethylene (LDPE) and ethyl vinyl acetate copolymer were successfully surface modified using synthesized BP1. FIGS. 4.3 and 4.4 also confirms the presence of coating on the given polymers.

The above chemistry provides a simple and facile way to graft terminal vinyl functionality onto different polymer surfaces and backbones with C—H functionality. The available vinyl groups on the surface can be used for further chemical modifications, cross-linking reactions, and other polymerization techniques.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A material having one of the following structures:

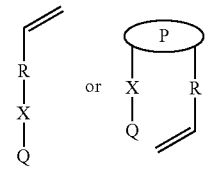

wherein Q is a photo cross-linkable moiety, X is selected from one of C, B, S, Al, Si, P, or Sn, wherein one or more additional moieties, H or an alkyl group are attached to X as needed to satisfy the normal valence of the atom represented by X, R is selected from: a substituted or unsubstituted alkyl, substituted or unsubstituted aryl, substituted or unsubstituted cycloalkyl, substituted or unsubstituted cycloalkenyl, substituted or unsubstituted biaryl, substituted or unsubstituted fused aryl, substituted or unsubstituted alkenyl, and substituted or unsubstituted alkynyl, or a combination of one or more of these, and semicircle P is selected from a polymer or a compound.

2. The material of claim 1, wherein the R group is selected from the group consisting of: hexane; heptane; octane; nonane; decane; undecane; dodecane; tridecane; tetradecane; pentadecane; hexadecane; heptadecane; octadecane; eicosane; heneicosane; docosane; tricosane; and a combination thereof.

3. The material of claim 1, wherein the photo cross-linkable moiety is selected from the group consisting of: an aryl ketone, an aryl azide group, a diazirine group, and a combination thereof.

4. The material of claim 3, wherein the aryl ketone is selected from the group consisting of: an acetophenone, an acetophenone derivative, a benzophenone, a benzophenone derivative, a naphtylmethylketone, a dinaphtylketone, a dinaphtylketone derivative, and a combination thereof.

5. The material of claim 1, wherein the polymer has a molecular weight of about 100 kilodaltons to 150 kilodaltons.

6. The material of claim 1, wherein the R group is selected from the group consisting of: hexane; heptane; octane; nonane; decane; undecane; dodecane; tridecane; tetradecane; pentadecane; hexadecane; heptadecane; heptadecane; octadecane; eicosane; heneicosane; docosane; tricosane; and a combination thereof, wherein at least one C—H bond has been replaced by an electronegative group selected from the group consisting of F, Cl, and Br.

7. The material of claim 1, wherein the polymer is a linear polyethylenimine polymer.

8. The material of claim 1, wherein the polymer is a branched polyethylenimine polymer.

9. The material of claim 1, wherein the molar ratio between R group and photo cross-linkable moiety can be a range from about 99:1 to 10:90.

10. The material of claim 1, wherein the vinyl moiety and the photo cross-linkable moiety are included in a structure selected from:

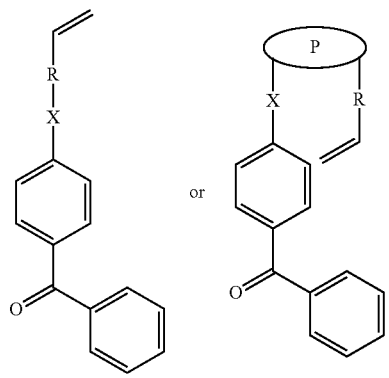

* * * * *